United States Patent [19]

(12) United States Patent
Katz et al.

(10) Patent No.: US 11,567,035 B2
(45) Date of Patent: Jan. 31, 2023

(54) RATIOMETRIC VAPOR SENSOR

(71) Applicant: THE JOHNS HOPKINS UNIVERSITY, Baltimore, MD (US)

(72) Inventors: Howard E. Katz, Owing Mills, MD (US); Hui Li, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 578 days.

(21) Appl. No.: 16/612,533

(22) PCT Filed: May 9, 2018

(86) PCT No.: PCT/US2018/031769
§ 371 (c)(1),
(2) Date: Nov. 11, 2019

(87) PCT Pub. No.: WO2018/208895
PCT Pub. Date: Nov. 15, 2018

(65) Prior Publication Data
US 2020/0200703 A1 Jun. 25, 2020

Related U.S. Application Data

(60) Provisional application No. 62/503,533, filed on May 9, 2017.

(51) Int. Cl.
*G01N 27/414* (2006.01)
*G01N 33/00* (2006.01)
(Continued)

(52) U.S. Cl.
CPC ..... *G01N 27/4143* (2013.01); *G01N 33/0037* (2013.01); *H01L 27/098* (2013.01); *H01L 27/283* (2013.01)

(58) Field of Classification Search
None
See application file for complete search history.

(56) References Cited

U.S. PATENT DOCUMENTS 4,776,203 A * 10/1988 Jones ................. G01N 27/4141
73/31.06
5,045,285 A * 9/1991 Kolesar, Jr. ........ G01N 27/4141
204/406

(Continued)

OTHER PUBLICATIONS

Besar, Kalpana, Jennifer Dailey, and Howard E. Katz. "Ethylene Detection Based on Organic Field-Effect Transistors With Porogen and Palladium Particle Receptor Enhancements." ACS applied materials & interfaces 9.2 (2017):1173-1177.
(Continued)

*Primary Examiner* — Erik Kielin
(74) *Attorney, Agent, or Firm* — Tarolli, Sundheim, Covell & Tummino LLP

(57) ABSTRACT

A ratiometric vapor sensor is described that includes a first sensor and a second sensor. The first sensor includes a first semiconductor component comprising a vapor-sensitive semiconducting organic compound, while the second sensor includes a second semiconductor component comprising a modified vapor-sensitive semiconducting organic compound including a modifying organic group. The ratiometric vapor sensor can be used to detect the presence of a vapor such as nitrogen dioxide, and determine the concentration of the vapor by comparing the outputs of electrodes connected to the first and second sensor.

23 Claims, 9 Drawing Sheets

(51) Int. Cl.
  *H01L 27/098* (2006.01)
  *H01L 27/28* (2006.01)

(56) References Cited

U.S. PATENT DOCUMENTS

2014/0352023 A1  12/2014  Mordecai et al.
2016/0157779 A1   6/2016  Baxi et al.
2018/0052136 A1*  2/2018  Diao ............... H01L 51/0533

OTHER PUBLICATIONS

Bujak, Piotr, et al. "Polymers for electronics and spintronics." Chemical Society Reviews 42.23 (2013): 8895-8999.
Choi, Seon-Jin, et al. "Optically Sintered 2D RuO2 Nanosheets: Temperature-Controlled NO2 Reaction." Advanced Functional Materials 27.13 (2017): 1606026.
Das, Arindam, et al. "A nitrogen dioxide sensor based on an organic transistor constructed from amorphous semiconducting polymers." Advanced Materials 19.22 (2007): 4018-4023.
Epifani, Mauro, et al. "Nanocrystalline Metal Oxides from the Injection of Metal Oxide Sols in Coordinating Solutions: Synthesis, Characterization, Thermal Stabilization, Device Processing, and Gas-Sensing Properties." Advanced Functional Materials 16.11 (2006): 1488-1498.
Esser, Birgit, Jan M. Schnorr, and Timothy M. Swager. "Selective detection of ethylene gas using carbon nanotube-based devices: utility in determination of fruit ripeness." Angewandte Chemie International Edition 51.23 (2012): 5752-5756.
Han, Shijiao, et al. "Poly (3-hexylthiophene)/polystyrene (P3HT/PS) blends based organic field-effect transistor ammonia gas sensor." Sensors and Actuators B: Chemical 225 (2016): 10-15.
He, Ming, et al. "Annealing effects on the photovoltaic performance of all-conjugated poly (3-alkylthiophene) diblock copolymer-based bulk heterojunction solar cells." Nanoscale 3.8 (2011): 3159-3163.
Huang, J., et al. "Response diversity and dual response mechanism of organic field-effect transistors with dinitrotoluene vapor." Journal of Materials Chemistry 20.13 (2010): 2644-2650.
Huang, Weiguo, et al. "Diverse Organic Field-Effect Transistor Sensor Responses from Two Functionalized Naphthalenetetracarboxylic Diimides and Copper Phthalocyanine Semiconductors Distinguishable Over a Wide Analyte Range." Advanced Functional Materials 23.33 (2013): 4094-4104.
Huo, Lijun, Yi Zhou, and Yongfang Li. "Alkylthio-substituted polythiophene: absorption and photovoltaic properties." Macromolecular rapid communications 30.11 (2009): 925-931.
Khim, Dongyoon, et al. "Precisely controlled ultrathin conjugated polymer films for large area transparent transistors and highly sensitive chemical sensors." Advanced Materials 28.14 (2016): 2752-2759.
Lv, Aifeng, et al. "Investigation into the Sensing Process of High-Performance H2S Sensors Based on Polymer Transistors." Chemistry—A European Journal 22.11 (2016): 3654-3659.
Marinelli, F., et al. "An organic field effect transistor as a selective NOx sensor operated at room temperature." Sensors and Actuators B: Chemical 140.2 (2009): 445-450.
Matsuguchi, Masanobu, Koji Tamai, and Yoshiro Sakai. "SO2 gas sensors using polymers with different amino groups." Sensors and Actuators B: Chemical 77.1-2 (2001): 363-367.
Mo, Daize, et al. "Alkyl functionalized bithiophene end-capped with 3, 4-ethylenedioxythiophene units: synthesis, electropolymerization and the capacitive properties of their polymers." Electrochimica Acta 151 (2015): 477-488.
Paek, Sunhee, et al. "Synthesis of Polythiophenes with Electron-Donating Side-Chain and their Application to Organic Thin-Film Transistors." Molecular Crystals and Liquid Crystals 504.1 (2009): 52-58.
Pernstich, K. P., et al. "Threshold voltage shift in organic field effect transistors by dipole monolayers on the gate insulator." Journal of Applied Physics 96.11 (2004): 6431-6438.
Ram, Manoj K., Ozlem Yavuz, and Matt Aldissi. "NO2 gas sensing based on ordered ultrathin films of conducting polymer and its nanocomposite." Synthetic Metals 151.1 (2005): 77-84.
Sen, Avijit, et al. "Liquid crystal-based sensors for selective and quantitative detection of nitrogen dioxide." Sensors and Actuators B: Chemical 178 (2013): 222-227.
Shaik, Mahabul, et al. "Sensitive detection of nitrogen dioxide gas at room temperature using poly (3,4-ethylenedioxythiophene) nanotubes." Journal of environmental chemical engineering 3.3 (2015): 1947-1952.
Siemons, Maike, Annika Leifert, and Ulrich Simon. "Preparation and Gas Sensing Characteristics of Nanoparticulate p-Type Semiconducting LnFeO3 and LnCrO3 Materials." Advanced Functional Materials 17.13 (2007): 2189-2197.
Sinha, Jasmine, et al. "Tetrathiafulvalene (TTF)-functionalized thiophene copolymerized with 3, 3?-didodecylquaterthiophene: synthesis, TTF trapping activity, and response to trinitrotoluene." Macromolecules 46.3 (2013): 708-717.
Takahashi, Masabumi, et al. "Palladium-catalyzed C—H homocoupling of bromothiophene derivatives and synthetic application to well-defined oligothiophenes." Journal of the American Chemical Society 128.33 (2006): 10930-10933.
Xie, Tao, et al. "Ammonia gas sensors based on poly (3-hexylthiophene)-molybdenum disulfide film transistors." Nanotechnology 27.6 (2016): 065502.
Yan, Yehan, et al. "Visualizing gaseous nitrogen dioxide by ratiometric fluorescence of carbon nanodots-quantum dots hybrid." Analytical chemistry 87.4 (2015): 2087-2093.
Zhang, Congcong, Penglei Chen, and Wenping Hu. "Organic field-effect transistor-based gas sensors." Chemical Society Reviews 44.8 (2015): 2087-2107.
Zhou, Chunshan, et al. "Printed thin-film transistors and NO2 gas sensors based on sorted semiconducting carbon nanotubes by isoindigo-based copolymer." Carbon 108 (2016): 372-380.

* cited by examiner

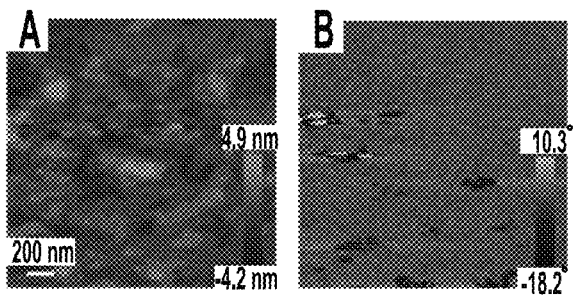
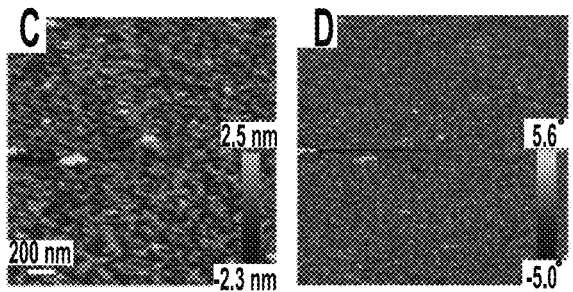
FIG. 4A  FIG. 4B
FIG. 4C  FIG. 4D
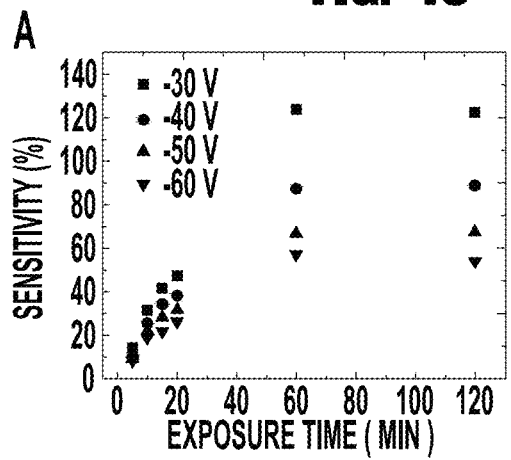
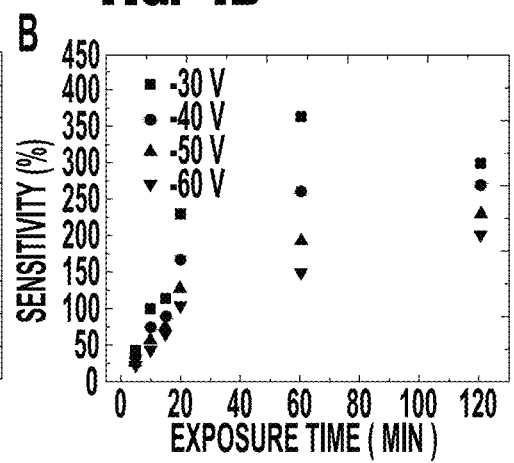
FIG. 5A  FIG. 5B
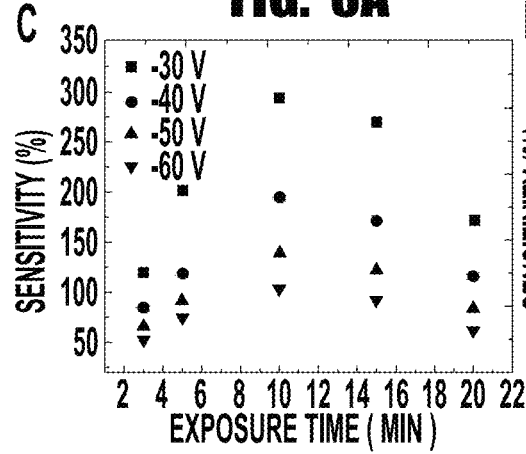
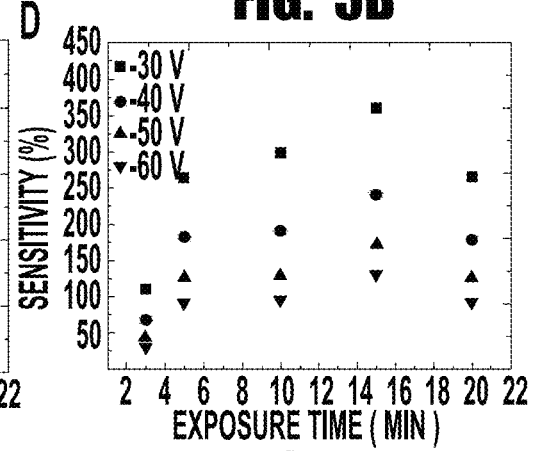
FIG. 5C  FIG. 5D

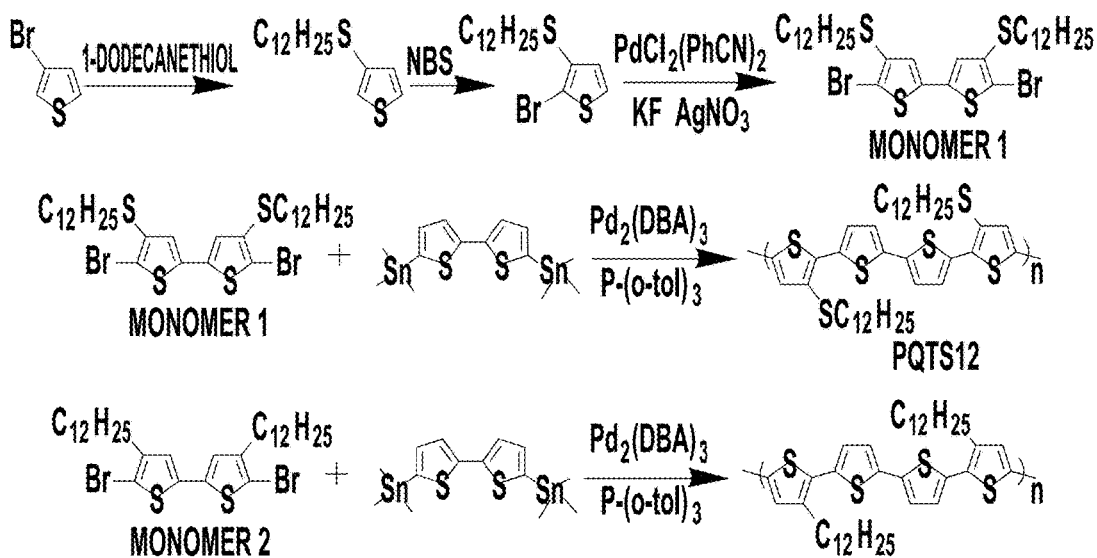
FIG. 8
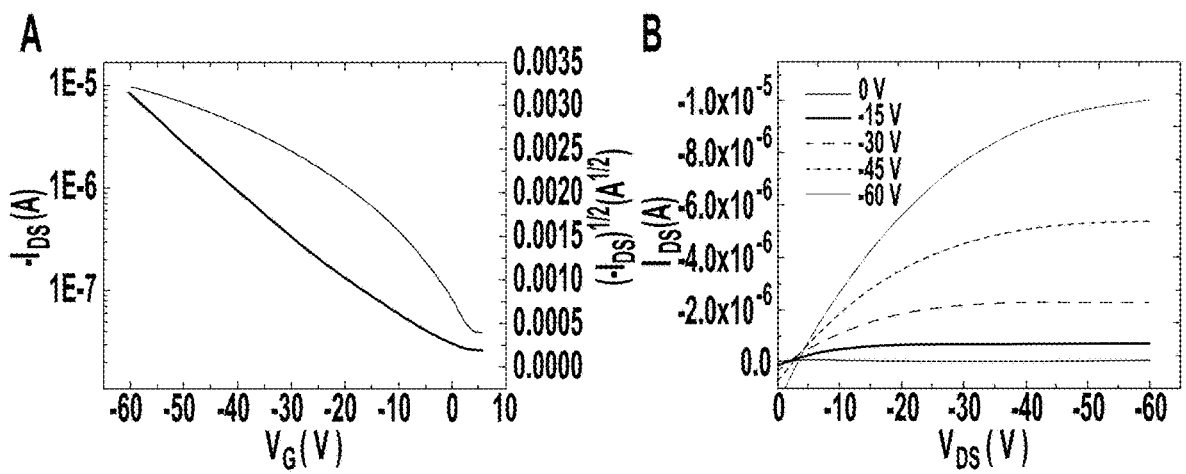
FIG. 9A     FIG. 9B
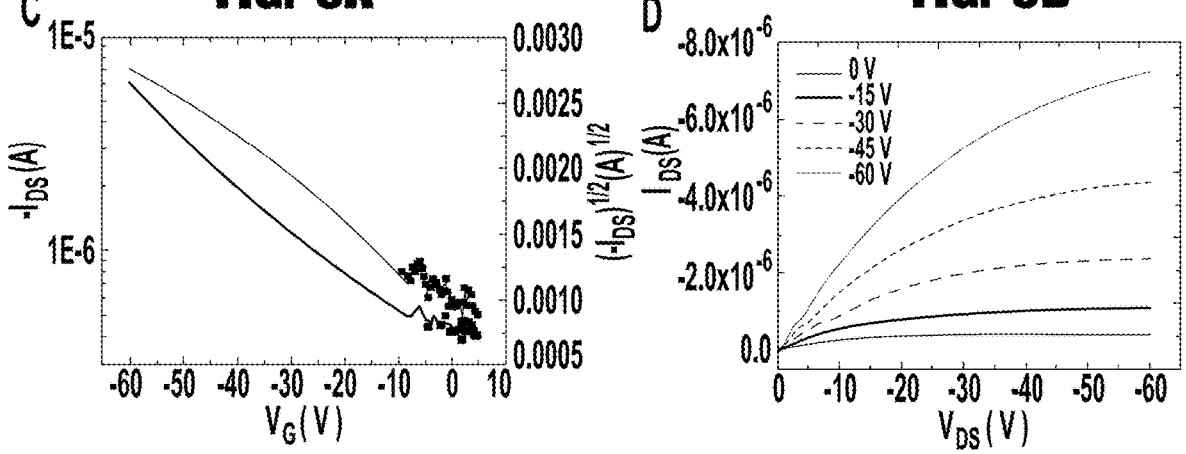
FIG. 9C     FIG. 9D

RATIOMETRIC VAPOR SENSOR

CROSS-REFERENCE TO RELATED APPLICATIONS

This application claims priority to U.S. Provisional Application Ser. No. 62/503,533, filed on May 9, 2017, which is hereby incorporated by reference in its entirety.

GOVERNMENT FUNDING

This invention was made with government support under grant number DE-FG01-07ER46465 awarded by the Department of Energy, and Assistance Agreement No. RD835871 awarded by the U.S. Environmental Protection Agency. The government has certain rights in this invention.

BACKGROUND

Nitrogen dioxide ($NO_2$) is one of most common toxic gases produced by combustion engines, and it is particularly relevant for health and safety in work and ambient environments when $NO_2$ concentrations reach the 1-10 ppm range. The exposure of this air pollutant has been known to cause various lung diseases and contributes to smog formation. Due to the increasing attention to environmental issues in recent years and the recognition of the variability of $NO_2$ concentrations across space and time, the sensing and detection of $NO_2$ has become a research focus.

Analytic methods like gas chromatography use passive badges to collect $NO_2$ and, as such, they are cumulative samples, measuring a total accumulated amount of $NO_2$ as a single output value, revealing little temporal evolution in concentrations. Furthermore, samples are expensive to analyze, limiting the number of samples that can be collected. Sensors have the potential to dramatically increase the resolution of $NO_2$ measurements at greatly decreased cost and may be small enough for deployment in homes or even as wearable personal samplers. Traditional chemiresistive sensors for $NO_2$ based on semiconducting oxides are operated at high temperature, which causes power consumption and possibly safety issues and thus restricts the wide application in room-temperature detection. Epifani et al., Adv. Funct. Mater., 16, 1488-1498 (2006); Siemons et al., Adv. Funct. Mater., 17, 2189-2197 (2007). Very recently, Il-Doo Kim et al. reported porous $RuO_2$ Nanosheets with sensitivity of 1.124% at 20 ppm at a film temperature of 80.3° C. Choi et al., Adv. Funct. Mater., 27, 1606026 (2017). Ratiometric sensing of $NO_2$ was also achieved by using inorganic materials. Sen et al., Sens Actuators B Chem., 178(1):222-227 (2013). For example, the concentration of $NO_2$ can be determined by ratiometric dual-color quantum dots. Yan et al., Analyt. Chem., 87, 2087-2093 (2015).

The high power requirements, possible toxicity, sensitivity to temperature and relative humidity, and drift of existing sensors limit the applicability of existing $NO_2$ sensors for long-term (weeks to months) deployment in homes or occupational environments. Less expensive and lower-power sensors that address these challenges, or provide early indications for when a shorter-term deployment of the high-power sensors would be needed, would allow a more complete characterization of exposures for health assessments considering variability in $NO_2$ concentrations.

Solution-processed semiconductors have been widely investigated in thin film devices because of their low cost, flexibility and room temperature operation. Bujak et al., Chem. Soc. Rev. 42, 8895-8999 (2013). A variety of solution-processed polymer materials have been explored for sensing gases such as the most reported ammonia ($NH_3$) (Khim et al., Adv. Mater., 28, 2752-2759 (2016); Han et al., Sensors and Actuators B: Chem., 225, 10-15 (2016)), sulfur dioxide ($SO_2$) (Matsuguchi et al., Sensors and Actuators B: Chem., 77, 363-367 (2001)), and $H_2S$ (Lv et al., Chemistry, 22(11), 3654-9 (2016)) which are all based on thin-film transistors. Other efforts, including adjusting the thickness of the sensing film (Esser et al., Angew. Chem. Int. Ed., 51, 5752-5756 (2012)), changing device structures (Zhang et al., Chem. Soc. Rev., 44, 2087-2107 (2015)), and using composite-materials by blending carbon nanotubes or different oxides (Tao et al., Nanotechnology, 27, 065502 (2016)) with polymer semiconductors have been made to further improve the sensitivity. Although few solution-processed organic materials were reported to detect $NO_2$ (Das et al., Adv. Mater., 19, 4018-4023 (2007); Marinelli et al., Sensors and Actuators B: Chem. 2009, 140, 445-450 (2009). the sensitivity is far lower than for other typical toxic gas sensors. Using composite materials is still the main strategy to enhance the sensitivity of $NO_2$ sensors (Zhou et al., Carbon, 108, 372-38 (2016)) due to the larger ratio of surface area to volume; the interaction mechanism in such materials can be difficult to define.

Thiophene polymers are successfully used in $NO_2$ sensors based on organic field-effect transistors (OFETs). For instance, regioregular polyhexylthiophene and its copolymer hybridized with $SnO_2$ were reported as an active layer to detect $NO_2$ (Ram et al., Synth. Met., 151, 77-84 (2005)) but they are not tailored to be selective for $NO_2$ gas. Although poly(3,4-ethylenedioxythiophene) (PEDOT) nanotube-based sensors showed good response towards sensing $NO_2$ at room temperature, good sensitivity (>50%) could only be achieved under relatively high concentration of $NO_2$ (>50 ppm). Shaik et al., J. Environ. Chem. Eng., 3, 1947-1952 (2015). Therefore, the development of simple and high-performance detectors sensing $NO_2$ concentrations in the 1-10 ppm range remains a challenge and needs further development.

An additional challenge is the development of OFET sensors capable of determining the concentration of an analyte. While the strength of a signal from an OFET sensor can vary in response to the concentration of an analyte, the strength of a signal from an OFET sensor can also be significantly affected by time of exposure, making these two causes for high signal strength difficult to distinguish. Accordingly, there remains a need for OFET sensors which are capable of not only detecting the presence of an analyte, but its concentration as well.

SUMMARY OF THE INVENTION

In one aspect, the present invention provides a ratiometric vapor sensor. The ratiometric vapor sensor includes a power source; a first sensor electrically connected to the power source, the first sensor comprising: a first semiconductor component comprising a vapor-sensitive semiconducting organic compound; a first input electrode electrically connected to the semiconductor component; and a second output electrode electrically connected to the semiconductor component; a second sensor electrically connected to the power source, the second sensor comprising: a second semiconductor component comprising a modified vapor-sensitive semiconducting organic compound including a modifying organic group; a second input electrode electrically connected to the semiconductor component; and a second output electrode electrically connected to the semiconductor component; and a gap in a surface of the first and second sensors that exposes the semiconductor material so that it can be contacted by a vapor.

In some embodiments, the first and second semiconductor components comprise a part of an organic field effect transistor. In further embodiments, the modified and unmodified vapor-sensitive semiconducting organic compounds are in contact with a silicon dioxide layer positioned over a silicon layer. In further embodiments, the vapor-sensitive semiconducting organic compound is a p-type organic semiconductor. In additional embodiments, the vapor-sensitive semiconducting organic compound includes an organic group selected from the group consisting of thiophene, phenylene, selenophene, fluorene, naphthalene, ethylene, ethynylene, cyclopentadiene, silacyclopentadiene, benzothiadiazole, benzoxadiazole, diketopyrroleopyrrole, and isoindigo. The modified vapor-sensitive semiconducting organic compound can be modified to include an electron-donating substituent or an electron-withdrawing substituent In another aspect, the invention provides a vapor-sensitive sensor, comprising: a power source; a vapor-sensitive semiconductor component electrically connected to the power source, the semiconducting component comprising a modified vapor-sensitive semiconducting organic compound including a modifying organic group; an input electrode electrically connected to the semiconductor component; and an output electrode electrically connected to the semiconductor component; a gap in a surface of the sensor that exposes the modified vapor-sensitive semiconducting organic compound including a modifying organic group so that it can be contacted by a vapor. In some embodiments, the modified vapor-sensitive semiconducting organic compound including a modifying organic group is poly(bisdodecylthioquaterthiophene) (PQTS12) and the vapor being detected is a nitrogen dioxide-containing vapor.

In another aspect, the invention provides a method of detecting and determining the concentration of a vapor using the ratiometric vapor sensor, comprising detecting the presence of a vapor if the voltage or current of the first output electrode or the second output electrode changes, and determining the concentration of a vapor by comparing the voltage or current of the first output electrode with that of the second output electrode to obtain a ratio, wherein the ratio is proportional to the concentration of the vapor.

BRIEF DESCRIPTION OF THE FIGURES

The present invention may be more readily understood by reference to the following drawings wherein:

FIGS. 4A-4D provide AFM height images and phase images of PQT12 film (a, b) and PQTS12 film (c, d) after annealing at 120° C. for 10 min. The resolution is 2 µm×2 µm.

FIGS. 5A-5D provide graphs showing the current changes measured under different exposure time with different gate voltages with $NO_2$ concentration being 1 ppm (a, b) and 5 ppm (c, d). PQT12: a, c; PQTS12: b, d.

FIG. 8 provides a scheme showing the synthetic procedures for PQT12 and PQTS12.

FIGS. 9A-9D provide graphs showing typical transfer ($V_{DS}$=−60 V) and output characteristics of field effect transistors based on PQT12 (a, b) and PQTS12 film (c, d).

Figure 1:
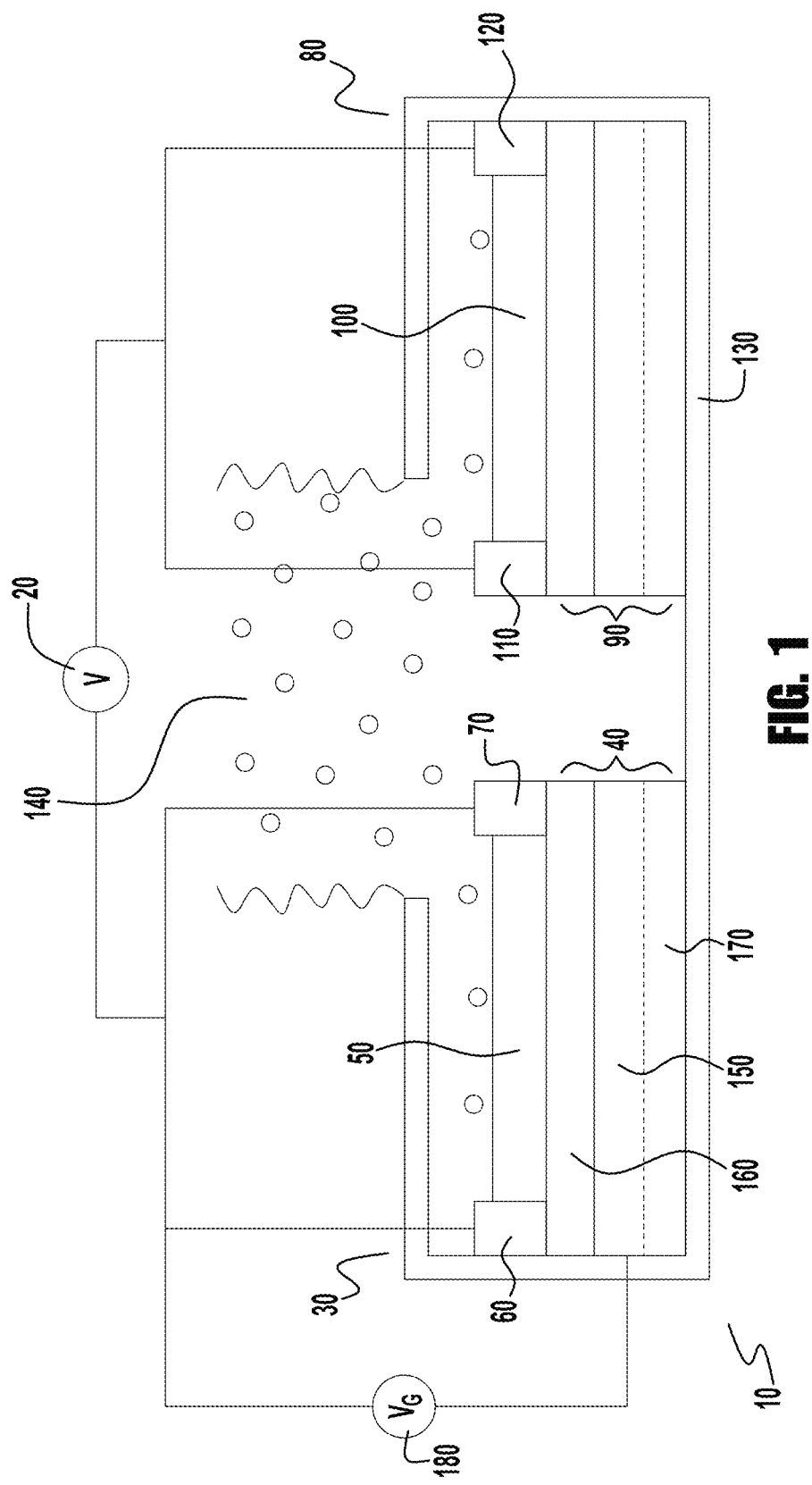
FIG. 1 provides a side view of a ratiometric vapor sensor.

To illustrate the invention, several embodiments of the invention will now be described in more detail. Reference will be made to the drawings, which are summarized above. Skilled artisans will recognize the embodiments provided herein have many useful alternatives that fall within the scope of the invention.

DETAILED DESCRIPTION OF THE INVENTION

The present invention provides a ratiometric vapor sensor, comprising: a power source; a first sensor electrically connected to the power source, the first sensor comprising: a first semiconductor component comprising a vapor-sensitive semiconducting organic compound; a first input electrode electrically connected to the semiconductor component; and a first output electrode electrically connected to the semiconductor component; a second sensor electrically connected to the power source, the second sensor comprising: a second semiconductor component comprising a modified vapor-sensitive semiconducting organic compound including a modifying organic group; a second input electrode electrically connected to the semiconductor component; and a second output electrode electrically connected to the semiconductor component; and a gap in a surface of the first and second sensors that exposes the semiconductor material so that it can be contacted by a vapor. The invention also includes methods of using the ratiometric vapor sensor to detect and determine the concentration of a vapor, and improved thiophene polymer-based vapor sensors.

Definitions

Unless otherwise defined, all technical and scientific terms used herein have the same meaning as commonly understood by one of ordinary skill in the art to which this invention pertains. In case of conflict, the present specification, including definitions, will control.

The terminology as set forth herein is for description of the embodiments only and should not be construed as limiting of the invention as a whole. Unless otherwise specified, "a," "an," ""the," and "at least one" are used interchangeably. Furthermore, as used in the description of the invention and the appended claims, the singular forms "a", "an", and "the" are inclusive of their plural forms, unless contraindicated by the context surrounding such.

The terms "comprising" and variations thereof do not have a limiting meaning where these terms appear in the description and claims.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for imidazopyridine derivatives are those that do not interfere with the compounds anticancer activity. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. A halo moiety can be chlorine, bromine, fluorine, or iodine.

Cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A heterocyclyl group means a mono- or bicyclic ring system in which one or more carbon atoms can be replaced by one or more heteroatoms such as, for example, 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

When a group is present more than once in any formula or scheme described herein, each group (or substituent) is independently selected, whether explicitly stated or not. For example, for the formula —C(O)—NR$_2$ each R group is independently selected. In addition, in some embodiments, a group is identified as being optional. An optional group may be entirely absent in some embodiments of the invention, but present in others.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

Ratiometric Vapor Sensors

In one aspect, the present invention provides a ratiometric vapor sensor 10. A side view of a ratiometric vapor sensor is provided in FIG. 1. A ratiometric vapor sensor is one that measures a ratio of current or voltage from the output electrodes of the vapor sensor (i.e. a ratiometric measurement) so that the concentration of a detected vapor can be determined. The ratiometric vapor sensor 10 includes a power source 20; a first sensor 30 electrically connected to the power source 20, the first sensor 30 comprising: a first semiconductor component 40 comprising a vapor-sensitive semiconducting organic compound 50; a first input electrode 60 electrically connected to the semiconductor component 40; and a first output electrode 70 electrically connected to the semiconductor component 40; a second sensor 80 electrically connected to the power source 20, the second sensor comprising: a second semiconductor component 90 comprising a modified vapor-sensitive semiconducting organic compound 100 including a modifying organic group; a second input electrode 110 electrically connected to the second semiconductor component 90; and a second output electrode 120 electrically connected to the second semiconductor component 90; and an optional enclosure 130 for the first 30 and second 80 sensors that includes a gap that exposes the semiconductor material so that it can be contacted by a vapor 140. In some embodiments, the sensors 30 and 80 are flexible.

In various embodiments, the vapor-sensitive semiconducting organic compound can function as a conductor or semiconductor as part of a simple resistor or a field-effect transistor. Accordingly, in some embodiments, the first and second semiconductor components comprise a part of an organic field effect transistor (OFET). In a field effect transistor, a gate electrode 150 is included, with an associated gate voltage source 180. In other embodiments, the first and second semiconducting components 40 or 90, the input electrodes 60 and 110, and the output electrodes 70 and 120 are in contact with a silicon dioxide layer 160 positioned over a silicon layer 170. A separate gate electrode 150 can be included in some embodiments, or the silicon layer 170 can be doped so that it can function as a gate electrode.

The ratiometric vapor sensor detects the presence of one or more vapors. A vapor is a compound that is diffused or suspended in the air. The compound can be diffused or suspended in the air as a result of being a gas, or can represent a suspension of material that is normally liquid or solid at normal temperatures (e.g., room temperature). In some embodiments, the ratiometric vapor sensor is sensitive to the vapors from nitrogen dioxide-containing compounds. Nitrogen dioxide-containing compounds are those including one or more nitro groups. Examples of nitrogen dioxide-containing compounds include explosive-derived vapors such as dinitrotoluene or trinitrotoluene vapor, and nitrogen dioxide gas. Organic field-effect sensors capable of detecting explosive-derived vapors have been developed. See Huang et al., J. Mater. Chem, 20, 2644-2650 (2010) and Sinha et al., Macromolecules, 46, 708-717 (2013). In some embodiments, the ratiometric vapor sensor is re-usable, so that it can be restored to a sensitive state after initial exposure to a vapor.

The Semiconductor Component

The ratiometric vapor sensor includes a semiconductor component, which electrically responds to the presence of a vapor. The semiconductor component is typically a thin layer of semiconducting organic material that can include other features such as pores or transition metal particles to increase the effectiveness of the semiconducting organic material. The semiconducting organic material can be deposited in a thin layer using methods such as spincoating and printing. In some embodiments, the layer of material is from 20 to 200 nm thick, while in other embodiments the layer of material is from 50 to 200 nm thick, or 20 to 100 nm thick.

The ratiometric vapor sensor can include a variety of different semiconducting organic compounds. In some embodiments, the semiconducting organic compound is a p-type organic semiconductor. In further embodiments, the semiconducting organic compound includes an organic group selected from the group consisting of thiophene, phenylene, selenophene, fluorene, naphthalene, ethylene, ethynylene, cyclopentadiene, silacyclopentadiene, benzothiadiazole, benzoxadiazole, diketopyrroleopyrrole, and isoindigo. These organic groups can form part of an organic small molecule, or part of a polymer. In additional embodiments, the semiconducting organic compound is a semiconducting polymer. For example, in some embodiments the vapor-sensitive semiconducting organic compound is poly(bisdodecylquaterthiophene) (PQT12) and the modified vapor-sensitive semiconducting organic compound is poly (bisdodecylthioquaterthiophene) (PQTS12).

The second sensor of the ratiometric vapor sensor includes a modified vapor-sensitive semiconducting organic compound including a modifying organic group. The vapor-sensitive semiconducting organic compound that serves as the base of the modified vapor sensitive semiconducting organic compound should be the same compound used in the first sensor. This modified organic compound results in a sensor which responds differently to the presence of the vapor of interest in comparison with the non-modified organic compound in the first sensor. The modifying organic compound can be an electron-donating substituent or an electron-withdrawing substituent. In some embodiments, the electron-donating substituent selected from the group consisting of alkylamino, cycloalkylamino, arylamino, alkoxy, cycloalkoxy, aryloxy, alkylthio, cycloalkylthio, arylthio, alkylseleno, cycloalkylseleno, and arylseleno substituents. In other embodiments, the electron-withdrawing substituent selected from the group consisting of nitro, cyano, trifluoromethyl, fluoro, chloro, bromo, iodo, lower alkyl keto, aryl, cycloalkyl keto, aryl keto, lower alkyl ester, cycloalkyl ester, aryl ester, lower alkyl amide, cycloalkylamide, aryl amide, phosphine oxide, alkyl phosphonate, alkyl sulfoxide, and alkyl sulfone substituents.

The semiconducting organic compound is a conjugated organic or polymer semiconductor, and particularly the organic compounds known as metal phthalocyanines that have metal atoms as possible coordination sites, or a polymer such as PQT12. In some embodiments, the vapor-sensitive semiconducting organic compound is a p-type organic semiconductor, in which the dominant charge carriers are holes, while in other embodiments the vapor-sensitive semiconducting organic compound is an n-type organic semiconductor. Where the vapor is a nitrogen-dioxide containing compound, the nitrogen dioxide acts as a dopant for the semiconductor, resulting in an increase of the output current, while for n-channel semiconductors the electron withdrawing groups of the nitrogen dioxide can quench n-channel semiconductor to induce a decrease of both field-effect mobility and source-drain current of the device.

In some embodiments, the vapor-sensitive semiconductor component includes a porogen. Porogens are compounds that can be added to the semiconducting organic compound to introduce pores into the material, thereby increasing its surface area and the interaction area of the compound layer. For example, the porogen can be N-(tert-butoxy-carbonyloxy)-phthalimide or tert-butyl phenyl carbonate.

Electrodes

The ratiometric vapor sensor includes input and output electrodes, which are electrically connected to the semiconductor component of the first and second sensors, and typically are placed on opposite sides of the semiconductor component. The input electrode is electrically connected to the power source (e.g., a potentiostat). The output electrode is connected to a display, alarm, and/or processing module that evaluates or responds to the output signal from the ratiometric vapor sensor.

Electrode(s) are fabricated using the methods and materials known in the art. Non-limiting examples of electroconductive material suitable for electrode construction on the substrate layer include Copper, Nickel, Tin, Gold, Platinum, Stainless Steel, and conductive inks such as carbon ink or Ag ink. In some embodiments, the electrode(s) are thin sheets of metal that are placed in contact with the semiconducting organic compound. In other embodiments, other methods of constructing the electrodes on the macroporous layer can be used. Non-limiting examples of constructing the electrodes on the substrate layer include ion beam techniques, etching, and self-assembly.

Enclosure for the Ratiometric Vapor Sensor

In some embodiments, the ratiometric vapor sensor is held within an enclosure. The enclosure provides support and protection for the invention, while including an opening to assure that the semiconductor material is at least partially exposed such that it can be contacted by a vapor. The enclosure should also provide access to the circuitry contacting the input and output electrodes, and possible circuitry to connect the sensor with a processing module. In some embodiments, both the first and second sensors of the ratiometric vapor sensor are held within a single enclosure, while in other embodiments the first and second sensors are held in separate first and second enclosures.

The enclosure may be formed of any suitable material or combination of suitable materials. Suitable materials may include elastomers, such as polydimethylsiloxane (PDMS); plastics, such as acrylic, polystyrene, polypropylene, polycarbonate, polymethyl methacrylate, etc.; glass; ceramics; sol-gels; silicon and/or other metalloids; metals or metal oxides; etc.

The enclosure for the ratiometric vapor sensor may be fabricated by any suitable mechanism, based on the desired application for the system and on materials used in fabrication. In some embodiments, the enclosure and its features can be fabricated using a water jet cutter. In other embodiments, one or more components may be molded, stamped, and/or embossed using a suitable mold. Such a mold may be formed of any suitable material by micromachining, etching, soft lithography, material deposition, cutting, and/or punching, among others. Alternatively, or in addition, components of the enclosure may be fabricated without a mold by etching, micromachining, cutting, punching, and/or material deposition.

Processing, Display, and Alarm Functions

In various embodiments, a processing module is included with the vapor-sensitive sensor. The processing module receives data from the sensor via conventional circuitry. In one embodiment, the processing module compares the detection data against expected characteristic transistor responses and indicates when they do not match. The processing module may be embodied as a central processing unit (CPU), a microcontroller, a microprocessor, a digital signal processor (DSP), a state machine, a programmable logic device, an application specific integrated circuit (ASIC), a general-purpose computing device, or other device known in the art.

The vapor sensor can include digital hardware (e.g., comprising a computer with a processor and memory, a digital signal processor, a hand held device, and the like) receives the digital representation of the conditioned one or more analog signals, processes the digital representation, and optionally storing the digital representation in memory to store the data. In some embodiments, digital hardware may include computer or electronic code with one or more instructions that process (e.g., interpret, manipulate, combine, use for decision making, and so on) the digital representations of the one or more signals received from the electrodes of the vapor sensor. For example, digital hardware may use the one or more signals for displaying information or generating an alarm based on the detection and/or detection of a particular concentration of a vapor (e.g., $NO_2$).

In some embodiments, the vapor sensor includes a display screen. The display can display the result of a comparison of the voltage or current of the first output electrode with that of the second output electrode, which provides a ratio that indicates the concentration of a detected vapor. The display screen can provide a numeric or graphic representation that can be used to indicate if a vapor has been detected, and in some cases the concentration and identify of the detected vapor. An example of a display screen is a touch sensitive screen that allows the user to input data as well as view information. Alternately, data can also be depicted on a software application of a remote computing device paired with the vapor sensor.

In some embodiments, the vapor sensor includes an alarm. The alarm is a device for signaling the user of the sensor when pre-defined alarm thresholds within the sensor have been triggered. For example, the alarm can be set to trigger if a pre-defined concentration of nitrogen dioxide vapor is detected (e.g., 1 ppm of $NO_2$). The alarm consists of an intrusive signal to the user, such as a warning light or sound.

In some embodiments, the vapor sensor is a wearable sensor comprising attachment means. A wearable sensor is configured to be attachable to a user's body so that the sensor will be associated with the user's environment and be able to provide rapid feedback to the user if vapors of interest are detected by the vapor sensor. In some embodiments, the sensor comprises a flexible substrate that can take different shapes or sizes, such as a strap, a band, or the like. Attachment means for the vapor sensor include buckles, clips, connectors such as those having a male and female portion, magnetic connectors, laces, and the like that can be used to secure the vapor sensor to the user or the user's clothing. For examples of wearable sensors, see U.S. Patent Publication 2014/0352023 and U.S. Patent Publication 2016/0157779, the disclosures of which are incorporated herein by reference.

Non-Ratiometric Vapor Sensor

Another aspect of the invention is directed to more sensitive vapor sensors identified by the inventors. These vapor sensors can be used to detect vapors, but include only a single sensor and therefore are not ratiometric vapor sensors. Accordingly, this aspect of the invention is directed to a vapor-sensitive sensor, comprising: a power source; a vapor-sensitive semiconductor component electrically connected to the power source, the semiconducting component comprising a modified vapor-sensitive semiconducting organic compound including a modifying organic group; an input electrode electrically connected to the semiconductor component; and an output electrode electrically connected to the semiconductor component; a gap in a surface of the sensor that exposes the modified vapor-sensitive semiconducting organic compound including a modifying organic group so that it can be contacted by a vapor. In some embodiments, the modified vapor-sensitive semiconducting organic compound including a modifying organic group is poly(bisdodecylthioquaterthiophene) (PQTS12). In other embodiments, the vapor detected by the vapor sensor is a nitrogen-dioxide containing compound such as nitrogen dioxide.

Vapor Detection Using the Ratiometric Vapor Sensor

In another aspect, the invention provides a method of detecting and determining the concentration of a vapor using a ratiometric vapor sensor, as described herein. The method includes the steps of detecting the presence of a vapor if the voltage or current of the first output electrode or the second output electrode changes, and determining the concentration of a vapor by comparing the voltage or current of the first output electrode with that of the second output electrode to obtain a ratio, wherein the ratio is proportional to the concentration of the vapor.

The ratiometric vapor sensor can correspond to any of the embodiments of ratiometric vapor sensors described herein. For example, the method of detecting and determining the concentration of a vapor can be conducted using a ratiometric vapor sensor that includes a power source; a first sensor electrically connected to the power source, the first sensor comprising: a first semiconductor component comprising a vapor-sensitive semiconducting organic compound; a first input electrode electrically connected to the semiconductor component; and a second output electrode electrically connected to the semiconductor component; a second sensor electrically connected to the power source, the second sensor comprising: a second semiconductor component comprising a modified vapor-sensitive semiconducting organic compound including a modifying organic group; a second input electrode electrically connected to the semiconductor component; and a second output electrode electrically connected to the semiconductor component; and a gap in a surface of the first and second sensors that exposes the semiconductor material so that it can be contacted by a vapor.

In some embodiments, the semiconductor components of the ratiometric vapor sensor are part of a field effect transistor. In further embodiments, the semiconductor components of the vapor-sensitive sensor are semiconducting polymers. In further embodiments, the method of detecting and determining the concentration of a vapor includes the step of determining the amount of vapor detected. For example, the ratiometric vapor sensor can be capable of determining that a vapor concentration of 1 ppm or more, 5 ppm or more, or 10 ppm or more, 25 ppm or more, or 50 ppm or more, or 100 ppm or more of the vapor compound is present in the environment surrounding the ratiometric vapor sensor.

The method of determining the concentration of a vapor includes the step of comparing the voltage or current of the first output electrode with that of the second output electrode to obtain a ratio, wherein the ratio is proportional to the concentration of the vapor. The comparison can be carried out by a processor that is included in the sensor or is in communication with the sensor. The nature of the proportional relationship between the ratio and the concentration of the vapor can vary depending on the vapor-sensitive semiconducting organic component and its corresponding modified. The ratio of the electrode outputs can be displayed, and or the concentration of the vapor based on the ratio can be displayed, or compared to a predetermined value to activate an alarm.

An example has been included to more clearly describe particular embodiments of the invention. However, there are a wide variety of other embodiments within the scope of the present invention, which should not be limited to the particular example provided herein.

Example

Sensitive and Selective $NO_2$ Sensing Based on Alkyl- and Alkylthio-thiophene Polymer Conductance and Conductance Ratio Changes from Differential Chemical Doping Generally speaking, reducing the thickness of active layers or preparing nanostructures or porous structures in films enhances the interaction between semiconductor and analytes. Besar et al., ACS Appl. Mater. Inter., 9, 1173-1177 (2017). These are morphological effects that can introduce binding sites and/or charge carrier traps with which analytes can interact. The covalent structural modification of semiconductors is another efficient strategy to achieve the favorable microstructure for sensing.

Figure 2A:
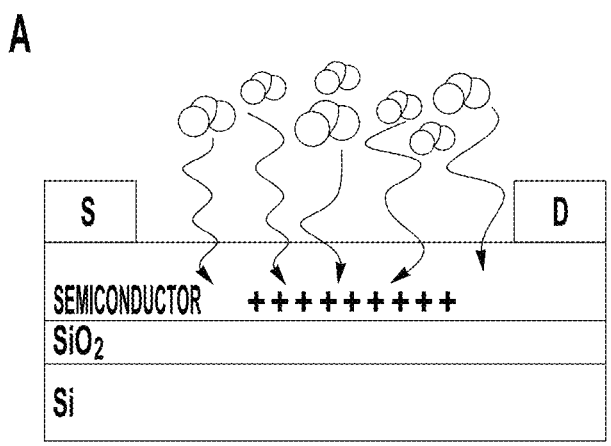
FIGS. 2A and 2B provide (a) a schematic diagram of the sensor structure, and (b) the chemical structures of polymer semiconductors.
Figure 2B:
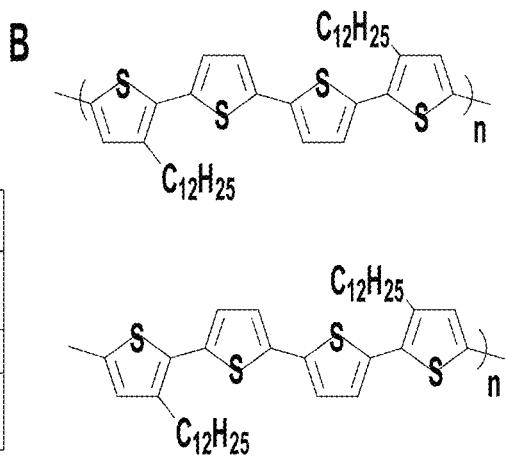

In this work, we introduce functionality to a semiconducting polymer to increase its likelihood of complexing and becoming oxidized (doped) by $NO_2$, thus increasing its current response relative to an unfunctionalized analog. Two thiophene-based polymers, PQT12 and PQTS12, the latter containing sulfide groups adjacent to thiophene rings serving as a functionalized analog, were synthesized and compared in OFET configurations (FIG. 2). Based on cyclic voltammetry and OFET characteristics, we propose that the presence of sulfur increases the trap density and promotes redox interactions between the polymer and $NO_2$ molecules. As a result, PQTS12 OFETs show higher sensitivity than those of PQT12 and satisfactory selectivity for $NO_2$. Furthermore, the ratio of the responses of the two polymers varied inversely with the $NO_2$ concentration, making this ratio an additional marker for determining concentration during a dosimetric exposure measurement. This is the first demonstration of designed ratiometric sensing by two different active OFETs based on polymer semiconductors to gauge a vapor concentration.

Results and Discussion

Figure 7A:
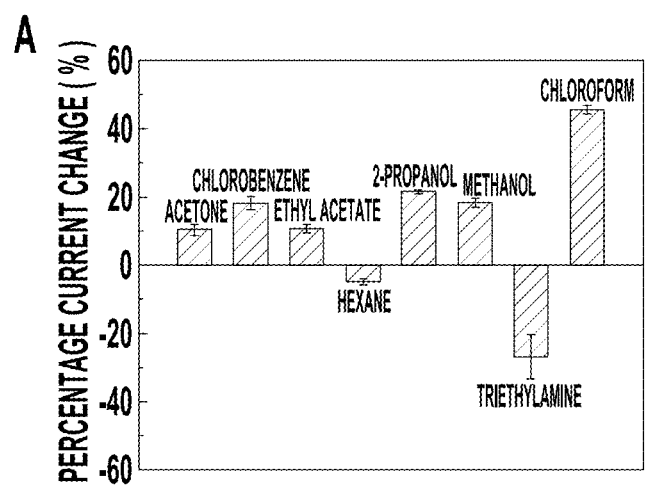
FIGS. 7A and 7B provide graphs showing the responses of $I_{DS}$ after exposure to common saturated solvent vapors on PQT12—(a) and PQTS12-based sensor (b) (VG=−30 V). acetone (16200 ppm); chlorobenzene (1050 ppm); ethyl acetate (8300 ppm); hexane (10400 ppm); 2-propanol (3800 ppm); methanol (11100 ppm); triethylamine (4500 ppm); chloroform (14000 ppm).
Figure 7B:
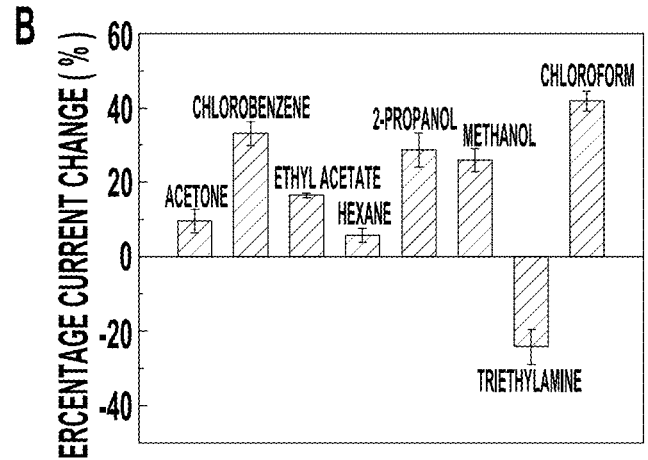
Figure 10A:
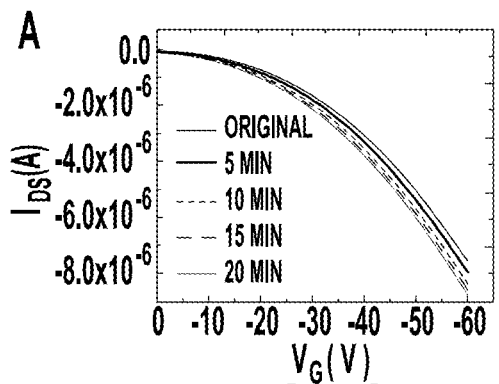
FIGS. 10A-10D provide graphs showing the air stability of transistor devices ($V_{DS}$=−60 V) based on PQT12 (a, b) and PQTS12 film (c, d).
Figure 10B:
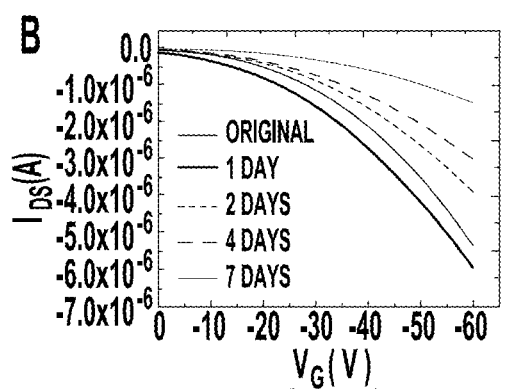
Figure 10C:
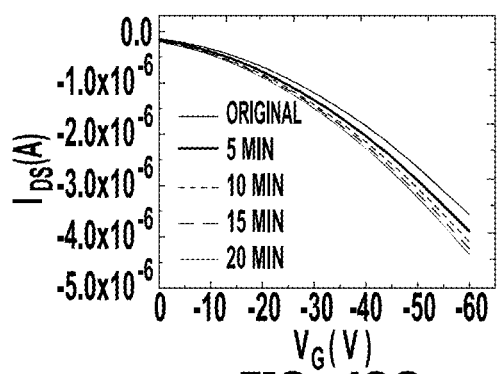
Figure 10D:
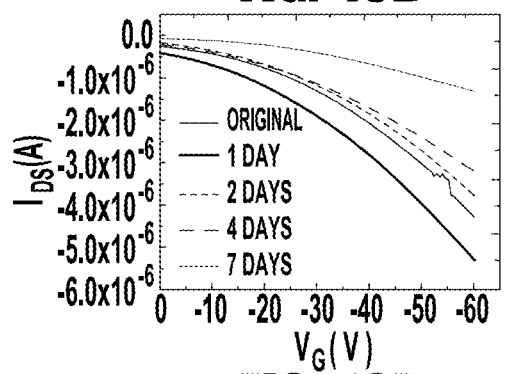
Figure 11A:
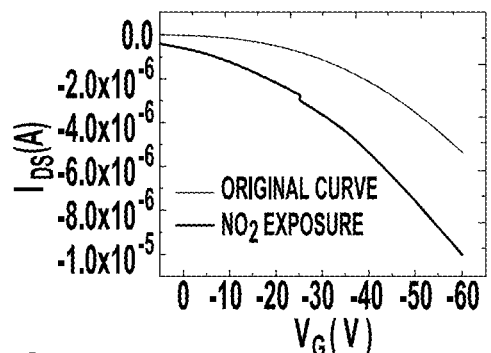
FIGS. 11A-11D provide graphs showing the transfer curves of transistor devices before and after $NO_2$ exposure based on PQT12 (a, b) and PQTS12 (c, d) under 1 ppm for 120 min (left) and 5 ppm for 15 min (right).
Figure 11B:
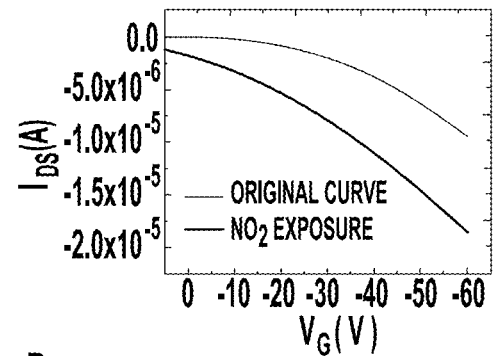
Figure 11C:
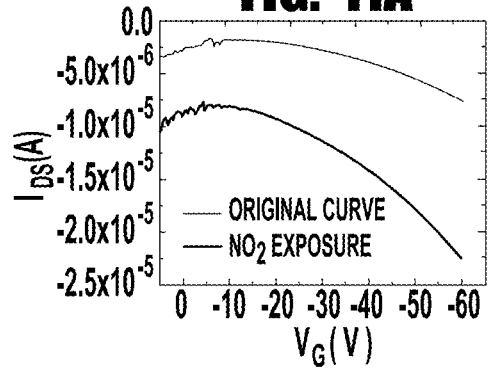
Figure 11D:
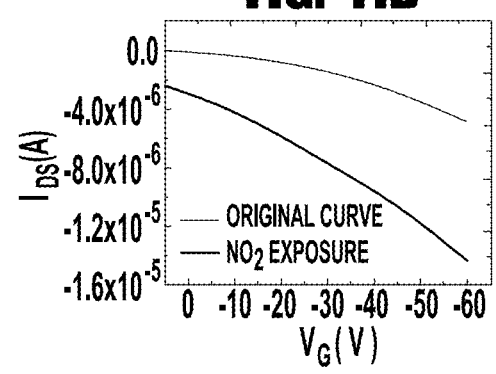
Figure 12A:
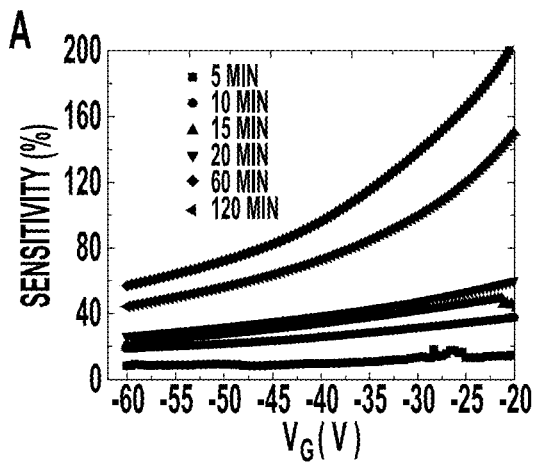
FIGS. 12A-12D provide graphs showing the sensitivity changes under different exposure time with different gate voltages with $NO_2$ concentration being 1 ppm (a, b) and 5 ppm (c, d). PQT12 film: a, c; PQTS12 film: b, d.
Figure 12B:
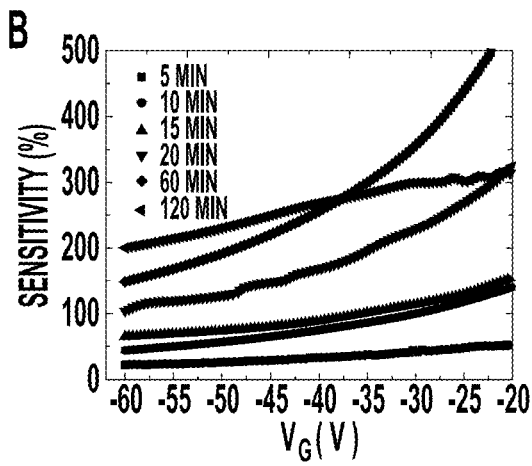
Figure 12C:
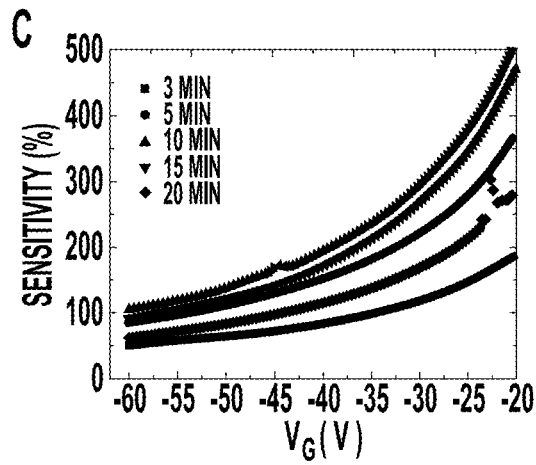
Figure 12D:
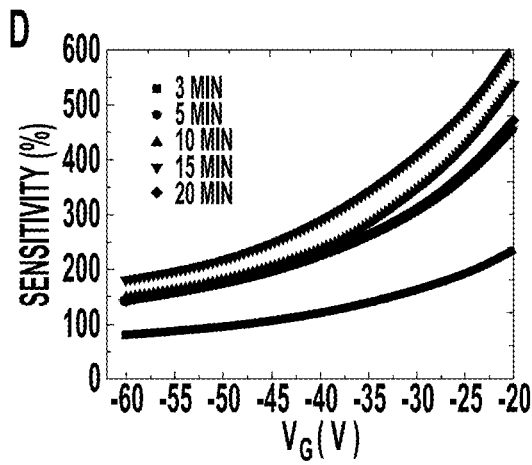

The first step in the synthesis of PQTS12 is the formation of 3-dodecylsulfanylthiophene by reaction of 3-bromothiophene with 1-dodecanethiol. Huo et al., Macromol. Rapid Commun., 30, 925-931 (2009). After bromination via N-bromosuccinimide, 2-bromo-3-dodecylsulfanylthiophene was obtained. Monomer 1 (5,5'-dibromo-4,4'-didodecylsulfanyl-2,2'-dithiophene) was obtained via palladium-catalyzed C—H homocoupling of 2-bromo-3-dodecylsulfanyl-thiophene. Takahashi, JACS, 128, 10930-10933 (2006). The synthetic procedures are shown in (FIG. 7). The polymerization of monomer 1 and 5,5'-bis(trimethylstannyl)-2,2'-bithiophene via Stille coupling reactions afforded crude dark red PQTS12. This synthetic method is different from the literature method reported by Sunhee Paek. Paek et al., Mol. Cryst. Liq. Cryst., 504, 52-58 (2009). Typical PQT12 polymer was also synthesized through the same synthetic procedures from 3-bromothiophene. The two polymers were purified by Soxhlet extraction. The low-molecular-weight portions and residual catalyst impurities were removed by dissolution in ethanol, acetone and hexane. The chloroform extracts were concentrated and precipitated in ethanol, and then the solids were collected as product. PQTS12 shows a number-average molecular weight (Mn) of 30 900 with a polydispersity index (PDI) of 1.8 and PQT12 has a lower molecular weight with Mn of 10 700 with a PDI of 1.2, as determined by gel permeation chromatography relative to polystyrene standards. The Differential scanning calorimetry (DSC) curves show that the PQT12 and PQTS12 exhibit endothermic peak at 118° C. and 190° C., respectively, corresponding to the melting of the backbones.

Figure 3A:
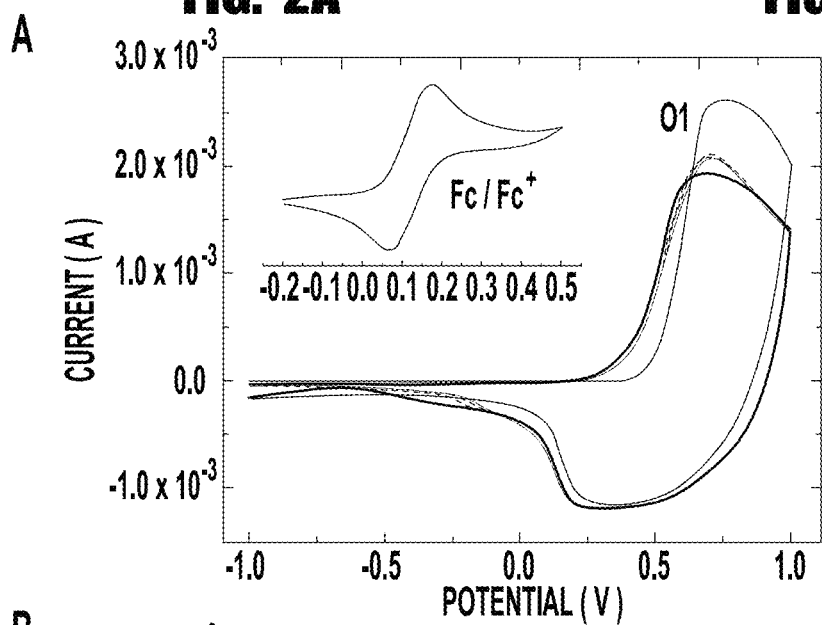
FIGS. 3A and 3B provides successive cyclic voltammograms of PQT12 film (a) and PQTS12 film (b) using dry $CH_3CN$ as solvent and 0.1 M n-$Bu_4NPF_6$ as a supporting electrolyte at a scan rate of 50 mV $s^{-1}$.
Figure 3B:
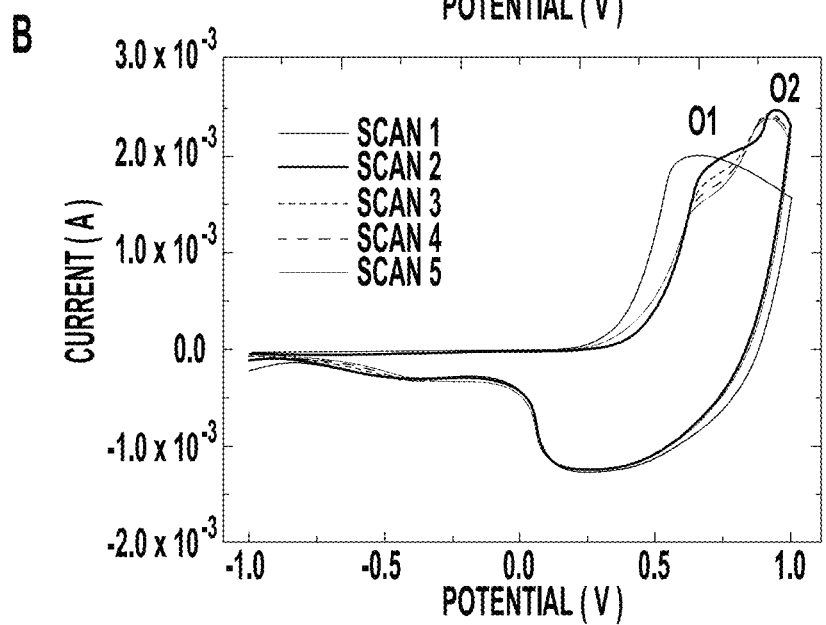

The electronic structures of the two polymers were investigated using cyclic voltammetry (CV) of thin films (FIG. 3). Ferrocene/ferrocenium (Fc/Fc$^+$) was used as an external standard, which was assigned an absolute energy of −4.8 eV vs vacuum level. There is reversible p-doping/dedoping in the positive potential range for PQT12 and PQTS12. PQTS12 possesses a lower onset oxidation potential (0.40 V) than that of PQT12 (0.45 V), indicating a modest electron-donating ability of the dodecylsulfanyl side-chain.

From the electrochemical oxidation doping results we can derive the HOMO levels of the PQTS12 and PQT12 as 5.04 eV and 5.09 eV, respectively. A sequence of five successive cyclic voltammograms of the two polymer films were taken to investigate film quality. We chose low potential (1.0 V) to avoid decomposing of polymers. We found for PQT12 that the first oxidation potentials (O1) are negatively shifted in later scans compared with the first scan. However, for PQTS12, the first oxidation potentials are positively shifted after the first scan which indicating PQTS12 film has been oxidized. For PQT12 film, we obtained a stable electrochemical behavior after the second scan. But there is a new peak (O2) that appears in the PQTS12 film after the second scan and the intensity of O1 decreases with the scan times. This might be due to the formation of new species as an intermediate which indicates the possibility of side reactions in the PQTS12 film. Generally, the negative shift of the oxidation potential suggests the decreased possibility of side reactions that modify the polymer making it more difficult to oxidize. Mo et al., Electrochim Acta, 151, 477-488 (2015). This indicates that the introduction of sulfur induces reactive sites in the PQTS12 film which are responsible for the positive shifts and side reactions during the electrochemical measurement.

Top-contact, bottom-gate architecture OFETs were fabricated as sensor devices. The polymer semiconductors were spin coated from a 4 mg mL$^{-1}$ chlorobenzene solution at 2000 rpm and then annealed at 120° C. for 10 min in the glove box. Au source/drain electrodes (W=8000 μm, L=250 μm) were used to measure the electrical performances of PQT12 and PQTS12-based devices. The field-effect mobilities were calculated from the transfer characteristics of more than 7 devices in the saturation region (VDS=−60 V). The original devices without gas exposure show typical p-type transport (FIG. 8). The transistors of PQT12 show a hole mobility of 0.027±0.004 cm$^2$ V$^{-1}$ s$^{-1}$, while PQTS12 films exhibit a hole mobility of 0.010±0.002 cm$^2$ V$^{-1}$ s$^{-1}$. The lower mobility of PQTS12 indicates the sulfurs in side chains impact the carrier transport in films. Tapping mode atomic force microscopy (AFM) was employed to analyze the morphology of PQT12 and PQTS12 thin film. As shown in FIG. 4, continuous thin film formation with large domains was observed in the PQT12 thin film, which provided efficient channels for the carrier transport. Smaller grains and numerous grain boundaries were observed in the PQTS12 thin film, which presumably promoted the trap activity and decreased the mobility. We calculate the trap densities using $N_{trap}=C_i\times|V_T-V_0|/e$, where $C_i$ is the capacitance per unit area (11.5 nF cm$^{-2}$), $V_T$ is threshold voltage and $V_0$ is turn-on voltage. For pure PQT12 film with thickness of 100 nm, the surface trap density is about $7.1\times10^{15}$ cm$^{-2}$. For pure PQTS12 film the value ($1.2\times10^{16}$ cm$^{-2}$) is higher than that of PQT12 film. Pernstich et al., J. Appl. Phys., 96, 6431-6438 (2004). This further confirms that more traps exist in PQTS12 film which is consistent with the result of CV.

Stability measurements of devices in air are presented in FIG. 10. The current of PQT12 increases only negligibly (2.5%) after 20 min in air, while the devices based on PQTS12 are somewhat more sensitive to moisture and oxygen on the tens of minutes time scale, the current increasing 21.7% after 20 min. The initial increase of current indicates that there are some gases in air that facilitate the carrier transport in the short term. On the days time scale, there is a slower but more substantial drift toward lower currents for both devices that could be compensated for by the use of referencing, as described below.

To measure responses to a given $NO_2$ concentration, we prepared twelve devices simultaneously, six of them as control devices and the others as sensing devices. As $NO_2$ gas was diluted by air that has the same humidity and components as the ambient atmosphere, the control devices were stored in air for the same time intervals as the exposure times for the sensing devices, and were used to calculate the effect of air on device current. According to the calculations for Limit of Blank (LOB) and Limit of Detection (LOD), we see that there is the possibility of up to about 45% sensitivity to blank for PQT12 film and 50% sensitivity to blank for PQTS12 film exposed in air, respectively (Table 1). That means the sensitivity of air below the value of LOD cannot be exactly determined and it is non-monotonic with exposure time because it is not significantly larger than the noise. We take these effects into account for the calculation of all sensitivities mentioned below, as a means of referencing, as the current increase contributed by house air was deducted from the total current increase after gas exposure. The sensor devices were tested after exposure to $NO_2$ gas, that is, OFETs were turned on after $NO_2$ exposure ended. All transistors showed significantly increased drain current when exposed to $NO_2$ gas. The transfer curves of optimized devices are shown in FIG. 11. Change in drain current (ΔI) was used as a measure of the sensitivity of these devices, calculated by the formula $100\%\times(I_{DS,NO2}-I_{DS,air}-\Delta I_{reference})/I_{DS,air}$, where $I_{DS,NO2}$ is the drain current after exposure of $NO_2$, $I_{DS,air}$ is the drain current before exposure $NO_2$ and $\Delta I_{reference}$ is the current increase of control device exposed in air with the same time intervals as sensing device.

TABLE 1

Limit of Blank and Limit of Detection for Control Devices

|  | PQT12-control | | PQTS12-control | |
| --- | --- | --- | --- | --- |
| 1 ppm | LOB | LOD | LOB | LOD |
| 5 min | 17.0% | 21.7% | 32.9% | 36.2% |
| 10 min | 4.5% | 8.0% | 48.1% | 56.9% |
| 15 min | 2.4% | 5.7% | 39.8% | 49.9% |
| 20 min | 5.8% | 10.8% | 42.9% | 63.2% |
| 60 min | 29.2% | 38.9% | 46.7% | 75.8% |
| 120 min | 19.5% | 32.3% | 12.1% | 24.5% |
| average | | 19.6% | | 51.1% |

|  | PQT12-control | | PQTS12-control | |
| --- | --- | --- | --- | --- |
| 5 ppm | LOB | LOD | LOB | LOD |
| 3 min | 32.9% | 45.9% | 45.8% | 53.4% |
| 5 min | 31.6% | 50.1% | 22.2% | 40.6% |
| 10 min | 23.0% | 36.9% | 42.5% | 56.9% |
| 15 min | 27.0% | 52.5% | 29.5% | 55.3% |
| 20 min | 34.1% | 43.4% | 35.5% | 45.9% |
| average | | 45.8% | | 50.4% |

Figure 13:
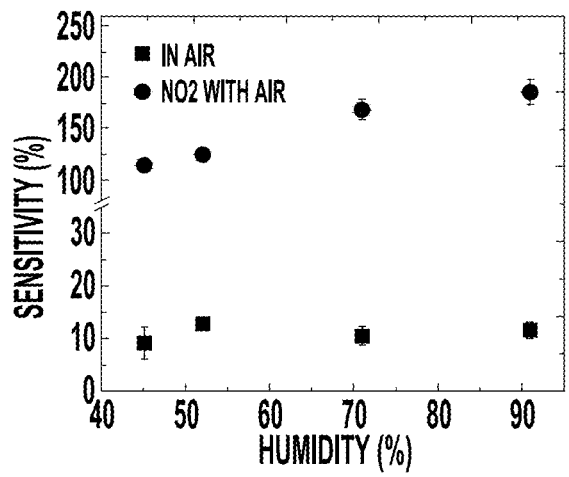
FIG. 13 provides a graph showing the effect of humidity on sensor based on PQTS12 film with 5 ppm $NO_2$ for 5 min ($V_G$=−60 V).

The responses of currents change with gate voltages. As shown in FIG. 12, the sensitivities of both PQT12 and PQTS12 decrease with the increase of gate voltage. That means these sensors are endowed with much higher sensitivity under lower gate voltage. FIG. 4 displays the responses of OFETs with gate voltage of −30 V, −40 V, −50 V and −60 V, respectively. We choose these voltages to eliminate the noise from instability near the threshold voltage. All plots in the figure show the average values from 4 or 5 devices. Clearly, PQTS12 show higher response under the same exposure conditions. In addition, the time to saturation for PQT12 film is somewhat shorter, indicating weaker total response capability for PQT12. With gate voltage of −30 V, the sensors based on PQTS12 films exhibit quite high sensitivity up to 360% and 410% under 1 ppm for 60 min and 5 ppm for 15 min, respectively, which are unusually high responses among polymer semiconductors interacting with $NO_2$. Meanwhile, the sensors based on PQT12 films show highest sensitivity of 120% and 270%, respectively, under the same conditions. We noted that the average ratio between the sensitivities of PQTS12 and PQT12 (R=sensitivity(PQTS12)/sensitivity(PQT12)) vary with the concentration of $NO_2$. For 1 ppm $NO_2$ gas concentration (FIG. 5a, b), the ratio is 3, while for higher $NO_2$ gas concentration, 5 ppm, this value is about 1.5. The data are collected in Table 2. This suggests the possibility that the concentration of gas could be detected by the ratio of sensitivity used in conjunction with the proportional current changes. The resultant responses with gate voltages of −40 V and −50 V give satisfactory sensitivities, while the gate voltage of −60 V gives lowest sensitivity among the gate voltages that we examined. The average sensitivity is about 200% for PQTS12 film exposed to 1 ppm $NO_2$ for 120 min at this gate voltage, which is still a high response compared to previously reported results. The average sensitivity for PQT12 film is 60% under the same conditions. Under 5 ppm exposure, the average sensitivity is up to 180% for PQTS12 film, but this value is reached after only 15 minutes' exposure. $NO_2$ can react with oxygen and water. We also tested the effect of humidity on the sensing of $NO_2$ by a PQTS12 film (FIG. 13, Table 3). The current slightly increases under wet air without $NO_2$, but the sensitivity continuously increases under $NO_2$ with higher humidity, which can be ascribed to the oxidizability of intermediates or the resultant $HNO_3$ from the $NO_2/O_2/H_2O$ reaction. In practical use, a separate calibration of humidity level would add further precision to determinations of $NO_2$ exposure.

TABLE 2

The sensitivity of sensors and control devices with different exposure time (VG = −40 V, −50 V and −60 V; all sensitivities are the average values collected from 4-6 devices.)

| Exposure time (min) | PQT12- control | PQT12- $NO_2$ | PQTS12- control | PQTS12- $NO_2$ | R |
|---|---|---|---|---|---|
| −40 V | | | | | |
| 1 ppm 5 | 13.5% | 9.9% | 21.5% | 33.4% | 3.4 |
| 10 | 3.0% | 25.5% | 40.3% | 74.0% | 2.9 |
| 15 | 1.1% | 34.2% | 35.3% | 88.8% | 2.6 |
| 20 | 3.9% | 38.1% | 34.0% | 167.8% | 4.4 |
| 60 | 21.5% | 87.4% | 38.7% | 260.4% | 3.0 |
| 120 | 15.2% | 88.7% | 10.7% | 269.1% | 3.0 |
| 5 ppm 3 | 22.2% | 84.0% | 42.9% | 117.2% | 1.4 |
| 5 | 21.6% | 118.6% | 8.8% | 232.3% | 1.9 |
| 10 | 17.2% | 194.4% | 34.0% | 239.8% | 1.2 |
| 15 | 14.5% | 171.2% | 24.7% | 290.5% | 1.7 |
| 20 | 26.2% | 145.7% | 27.9% | 219.3% | 1.5 |
| −50 V | | | | | |
| 1 ppm 5 | 12.1% | 9.1% | 17.7% | 26.9% | 3.0 |
| 10 | 2.3% | 21.6% | 35.2% | 56.9% | 2.6 |
| 15 | 1.0% | 28.2% | 33.0% | 75.1% | 2.7 |
| 20 | 3.3% | 31.6% | 29.2% | 127.5% | 4.0 |
| 60 | 16.6% | 66.9% | 35.1% | 193.2% | 2.9 |
| 120 | 12.1% | 67.3% | 10.3% | 230.8% | 3.4 |
| 5 ppm 3 | 17.1% | 65.4% | 38.7% | 94.2% | 1.4 |
| 5 | 18.1% | 95.7% | 8.6% | 176.3% | 1.8 |
| 10 | 14.8% | 138.9% | 29.0% | 179.2% | 1.3 |
| 15 | 8.5% | 122.1% | 22.5% | 221.8% | 1.8 |
| 20 | 21.4% | 99.3% | 24.2% | 170.9% | 1.7 |
| −60 V | | | | | |
| 1 ppm 5 | 8.6% | 8.5% | 13.9% | 22.7% | 2.7 |
| 10 | 4.0% | 18.9% | 31.4% | 48.1% | 2.5 |
| 15 | 1.8% | 21.8% | 26.5% | 66.1% | 3.0 |
| 20 | 3.2% | 26.4% | 25.0% | 104.3% | 4.0 |
| 60 | 7.9% | 57.2% | 34.7% | 150.3% | 2.6 |
| 120 | 10.9% | 57.9% | 10.7% | 201.7% | 3.5 |
| 5 ppm 3 | 11.1% | 52.9% | 25.5% | 80.4% | 1.5 |
| 5 | 19.8% | 77.7% | 8.8% | 141.6% | 1.8 |
| 10 | 10.7% | 103.1% | 25.2% | 146.5% | 1.4 |
| 15 | 6.1% | 97.9% | 20.7% | 181.4% | 1.8 |
| 20 | 19.7% | 72.0% | 22.4% | 122.4% | 1.7 |

TABLE 3

The sensitivity of sensors based on PQTS12 film without $NO_2$ and with 5 ppm $NO_2$ for 5 min under different humidity levels ($V_G$ = −60 V).

| Humidity | 45% | 52% | 71% | 91% |
|---|---|---|---|---|
| in air | 9.2% ± 3.1% | 12.9% ± 1.1% | 11.6% ± 0.7% | 11.9 ± 0.5% |
| $NO_2$ with air | 114.7% ± 6% | 124.4% ± 4.1% | 169.0% ± 10.1% | 185.8% ± 12.3% |

Figure 6:
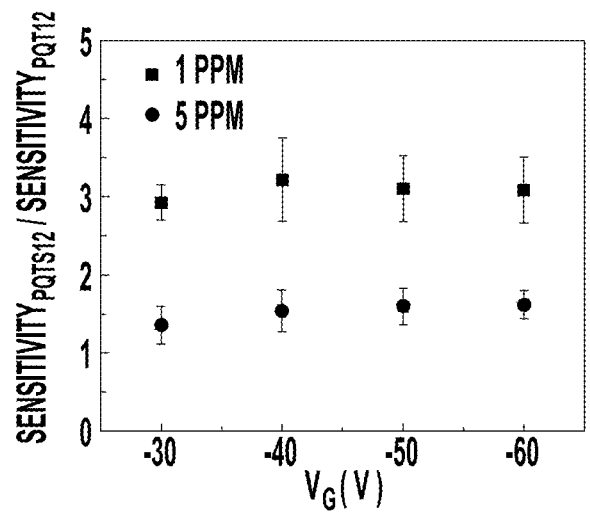
FIG. 6 provides a graph showing the sensitivity ratio of PQTS12 and PQT12 with different gate voltages with $NO_2$ concentration being 1 ppm and 5 ppm.

We also calculated the ratios between the sensitivities of PQTS12 and PQT12 when the gate voltage was set to be −40 V, −50 V and −60V. Again, we find the results follow the rules mentioned above; that is, the ratio of responses of PQTS12 and PQT12 is 3 and 1.5 under 1 ppm and 5 ppm, respectively, and insusceptible to gate voltages. The R values are collected in FIG. 6 and the data are shown in the supporting information. Besides 1 ppm and 5 ppm exposure, we also exposed the devices with 10 ppm $NO_2$ for 5 min, the average sensitivity is 195% and 229% for PQT12-based devices and PQTS12-based devices, respectively. The ratio of responses of PQTS12 and PQT12 is about 1.2. These results further demonstrate that this ratio can be used as a marker for determining concentration during a dosimetric exposure measurement.

Figure 14:
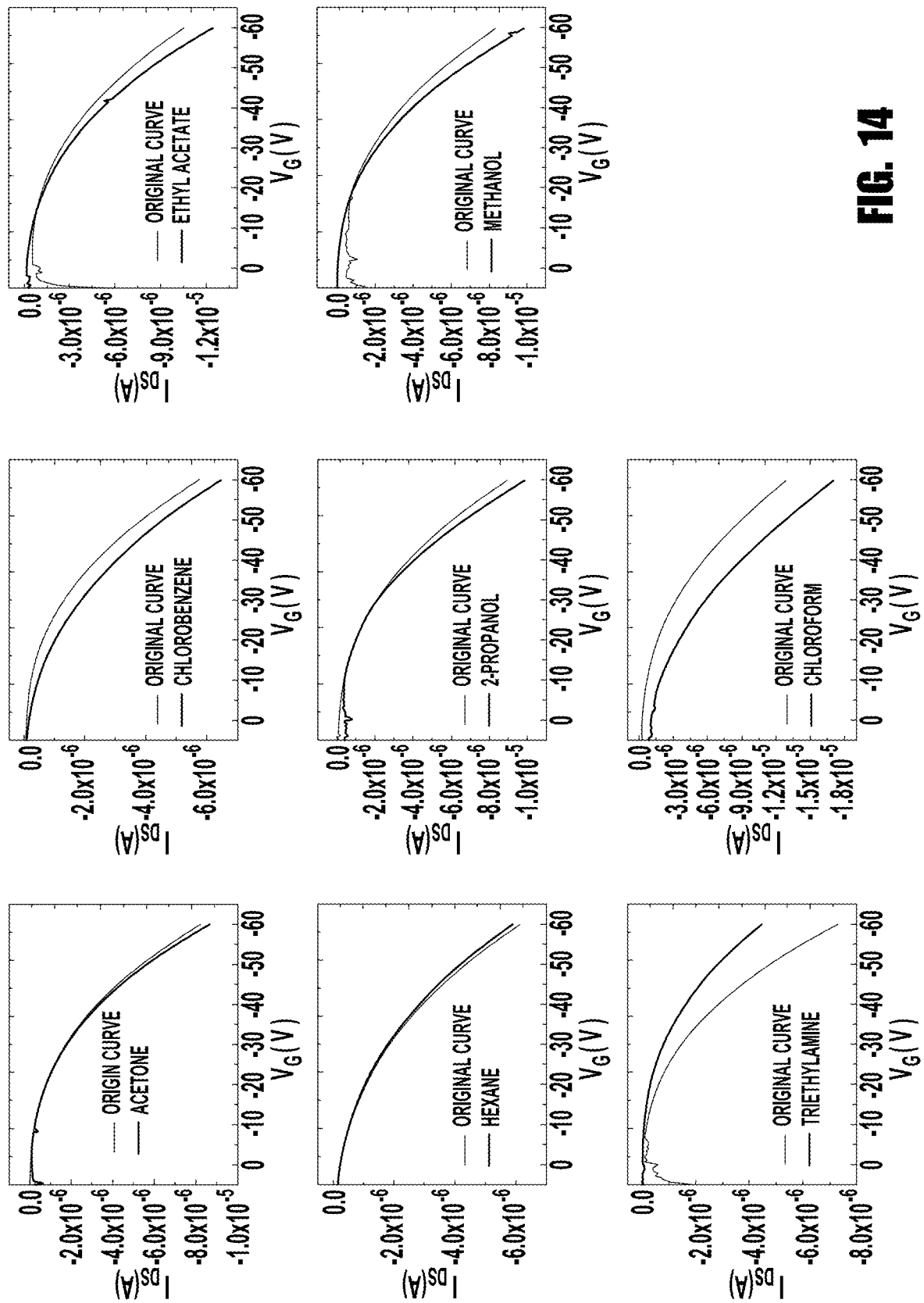
FIG. 14 provides graphs showing the transfer curves of transistor devices before and after solvent vapor exposure based on PQT12 film FIG. 15 provides graphs showing the transfer curves of transistor devices before and after solvent vapor exposure based on PQTS12 film.
Figure 15:
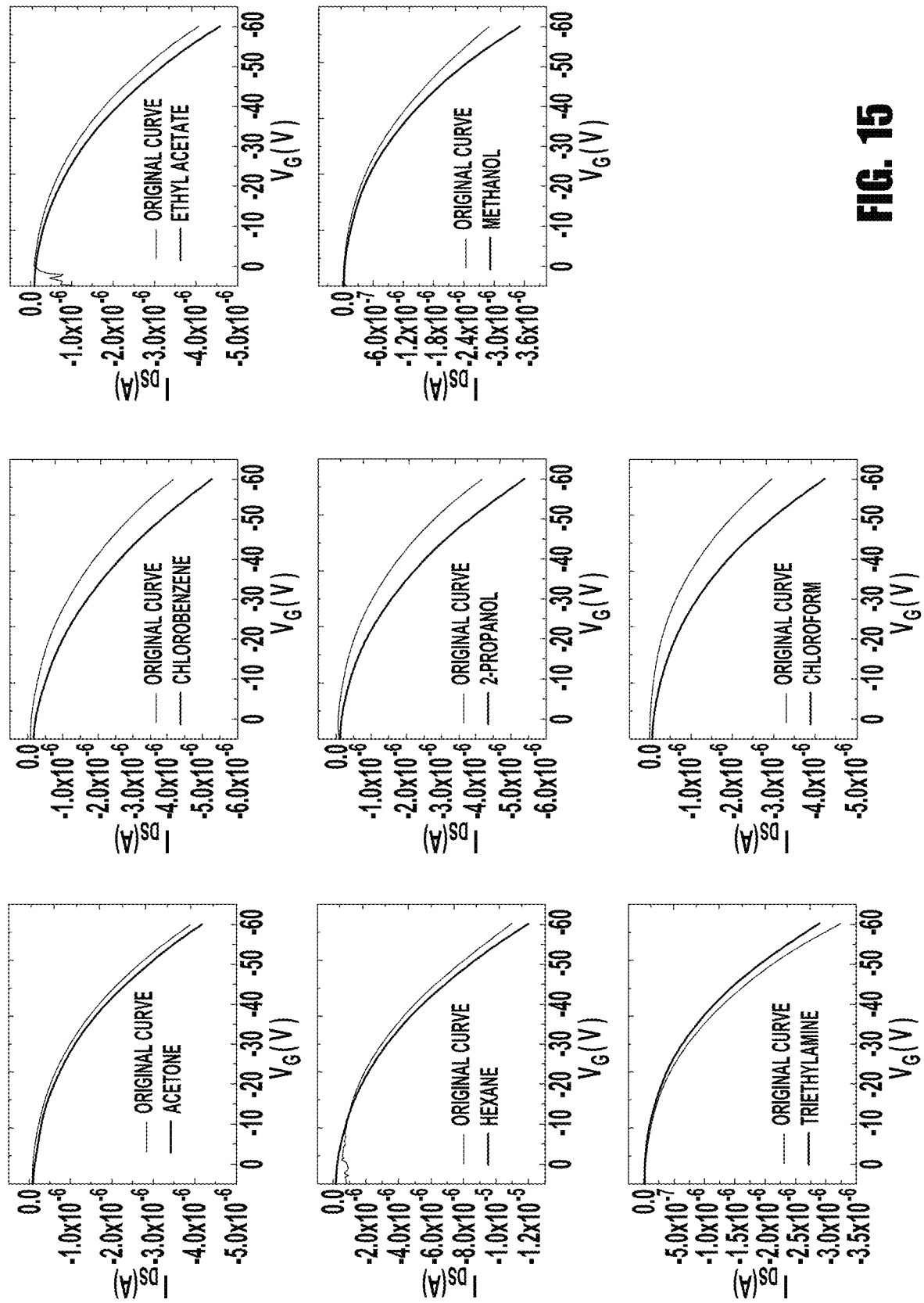

Selectivity studies of PQT12 and PQTS12 films were carried out by exposure to common saturated solvent vapors like acetone, chlorobenzene, hexane, ethyl acetate, methanol, 2-propanol, triethylamine and chloroform, as shown in FIG. 7. The transfer curves before and after vapor exposure are shown in FIGS. 14 & 15. The solvent vapor pressures being much higher than the $NO_2$ vapor pressures used in this study. Acetone could be considered a more Lewis basic carbonyl compound than atmospheric $CO_2$, while methanol is a carrier of OH groups at higher vapor pressure than atmospheric humidity. The data were obtained using a gate voltage of −30 V. For PQTS12 films, a large increase of $I_{DS}$ is observed after exposure to chlorobenzene and chloroform, which could possibly be attributed to the rearrangement of morphology analogous to saturated solvent vapor annealing treatment (He et al., Nanoscale, 3, 3159-3163 (2011)) or to HCl impurity in the film, which could be prefiltered using a weakly basic powder in a real application. Only chloroform vapor significantly affects the conductivity of the PQT12 film, and this may have been because of the HCl contaminant ubiquitously present in chloroform. Triethylamine gives a large decrease of $I_{DS}$ because of its electron-rich, trapping character as we and others have reported for amines in the past. Huang et al., Adv. Funct. Mater., 23, 4094-4104 (2013). Compared to PQT12, PQTS12 is a bit more sensitive to the alcohols, methanol, 2-propanol. Only minor changes to $I_{DS}$ are observed after exposure of this OFET to acetone, ethyl acetate and hexane, even as saturated vapors. Except for chloroform and triethylamine, we found that current decreases with high concentrations of other solvents and the current increases with low concentrations using PQT12 film. This indicates two possible mechanisms. At low concentrations, there is a synergistic interaction with oxygen or other impurities that slightly dopes the semiconductor or decreases grain boundary barriers. At higher (fully saturated) concentrations, the dipole quenching effect is more important, as many of the vapors caused current decreases.

CONCLUSION

Thiophene-polymers, PQT12 and PQTS12, are reported as $NO_2$ sensing materials for room-temperature detection. Thin films of PQTS12 show relatively lower hole mobility due to traps in films and smaller domain morphology based on cyclic voltammetry and AFM characterizations, respectively. PQTS12 shows higher response to $NO_2$ gas, with the highest observed sensitivity of 410% and satisfactory selectivity. Such high sensitivity and selectivity can be attributed to the incorporation of sulfurs in the side chains affecting both the electronic and morphological properties. The response ratio relative to PQT12 provides a means of distinguishing concentration level from exposure time effects on the responses.

Materials and Methods

Unless otherwise indicated, the starting materials were obtained from Sigma-Aldrich or Alfa Aesar and were used without further purification. $^1$H NMR (400 MHz) spectra were recorded on Bruker Avance spectrometer using $CDCl_3$ as solvent and tetramethylsilane (TMS) as the internal standard. Molecular weights were determined using gel permeation chromatography on a Waters 1515 Isocratic HPLC with a Waters 2489 UV/vis detector using polystyrene as standard and THF as eluent. Cyclic voltammetry (CV) was performed in a one-chamber, three-electrode cell in acetonitrile containing 0.1 M n-$Bu_4NPF_6$ as a supporting electrolyte. A glass carbon disk, a platinum wire and Ag/AgCl electrode, were used as the working electrode, auxiliary electrode and reference electrode, respectively. Atomic force microscopy images were taken in tapping mode using a Dimensional 3100 AFM (Bruker Nano, Santa Barbara, Calif.). The images were visualized using the Nanoscope software (Bruker). Gas sensing experiment was conducted by using the Environics 4040 Series Gas Dilution System.

Calculation of HOMO Level: Ferrocene/ferrocenium (Fc/$Fc^+$) was used as external reference. The redox potential of Fc/$Fc^+$ was assumed to have an absolute energy level of −4.80 eV to vacuum. The redox potential of Fc/$Fc^+$ was measured under the same conditions, and it is located at 0.16 V to the Ag/AgCl electrode. The energy levels of the highest occupied molecular orbital (HOMO) was calculated according to the equations: HOMO=−e($E_{ox}$+4.64) (eV), where $E_{ox}$ is the onset oxidation potential vs Ag/AgCl.

OFET Fabrication and Characterization: Top contact/bottom gate OFET devices were fabricated by using highly doped n doped silicon wafers with 300 nm silicon dioxide as substrates. The substrates were cleaned and modified with hexamethyldisilazane (HMDS) self-assembled monolayer. The polymers were dissolved in chlorobenzene with the concentration of 4 mg $mL^{-1}$. The thin films were prepared by spin coating the solution on the substrates. Then the polymer thin-film was annealed on a hot plate at 120° C. for 10 min under $N_2$ atmosphere. Gold contacts of 50 nm were deposited on the thin film as source and drain electrodes with a channel width of 8000 µm and a channel length of 250 µm. The electrical performance of transistors before and after exposure to gas was carried out using an Agilent 4155C Semiconductor Parameter analyzer in ambient. The mobility was calculated in the saturation regime according to the equation: $I_{DS}=(W/2 L)\mu C_i(V_G-V_T)^2$, where $I_{DS}$ is the drain current, µ is the mobility, and $V_G$ and $V_T$ are the gate voltage and threshold voltage, respectively.

Sensing Measurement: A home-made gas flow chamber was used for $NO_2$ exposure experiments. The chamber was blown by dry air for 10 min before the devices were placed inside. $NO_2$ gas and air were introduced through clean tubing and flowed through the Environics 4040 Series Gas Dilution System to obtain desired concentration. Devices were quickly transferred to the probe station after gas exposure. The control devices were stored in air for the same time intervals as the exposure times for the sensing devices.

Selectivity Measurement: A 200 mL well-sealed flask was used as a chamber for solvent exposure. Air was removed from the system using a syringe. Organic solvent was introduced into the chamber and kept for 10 min before a device was placed inside. The devices were exposed for 5 min under saturated solvent vapor, and then quickly transferred to a probe station to ensure immediate results.

Synthesis and Characterizations:

5,5'-Dibromo-4,4'-didodecylsulfanyl-2,2'-dithiophene (monomer 1): A solution of 2-bromo-3-dodecylsulfothiophene (1 g, 2.8 mmol) and DMSO (40 ml) was stirred at room temperature. 3 mol % of $PdCl_2(PhCN)_2$ (31.7 mg, 0.08 mmol), potassium fluoride (320 mg, 5.5 mmol) and silver (I) nitrate (935 mg, 5.5 mmol) were added in the solution successively. The mixture was heated at 60° C. and stirred overnight. Additional potassium fluoride (320 mg, 5.5 mmol) and silver (I) nitrate (935 mg, 5.5 mmol) were added and then the mixture was stirred for further 12 h. The final mixture was filtered through a Celite column and washed with diethyl ether. The filtrate was washed with water and the organic layer was dried over anhydrous $Na_2SO_4$ and concentrated under reduced pressure. The crude solid was purified by column chromatography to afford 760 mg of light yellow solid 1 (75%). $^1$H NMR ($CDCl_3$) δ 6.91 (s, 2H), 2.88-2.84 (t, 4H), 1.64-1.54 (m, 4H), 1.30-1.26 (m, 36H), 0.90-0.86 (t, 6H). FAB-HRMS: Calcd. for $[M+H]^+$: 724.82. Found: 724.20.

Synthesis of Monomer 2 is carried out in a similar procedure as monomer 1 using 2-bromo-3-dodecylthiophene with a yield of 67%. $^1$H NMR ($CDCl_3$) δ 6.91 (s, 2H), 2.88-2.84 (t, 4H), 1.64-1.54 (m, 4H), 1.31-1.25 (m, 36H), 0.90-0.86 (t, 6H). FAB-HRMS: Calcd. for $[M+H]^+$: 660.69. Found: 660.20.

Polymer PQTS12: 5,5'-Dibromo-4,4'-didodecylsulfanyl-2,2'-dithiophene (300 mg, 0.41 mmol) and 5,5'-bis(trimethylstannyl)-2,2'-bithiophene (204 mg, 0.41 mmol) were added into a Schlenk tube and subsequently dissolved in 6 mL of degassed chlorobenzene. The solution was purged with nitrogen for 10 min, and then $Pd_2(dba)_3$ (3 mol %) and P(o-tol)$_3$ (12 mol %) were added. The reaction mixture was stirred at 120° C. for 2 days. After being cooled to room temperature, the solution was precipitated in methanol and subjected to Soxhlet extraction successively in methanol, acetone, and hexane for the removal of oligomers and catalytic impurities, followed by collection in chloroform and precipitated in methanol again. The polymer was obtained as a metallic dark purple solid (348 mg, 85%).

Polymer PQT12: PQT12 is carried out in a similar procedure mentioned above by using 5,5'-dibromo-4,4'-didodecyl-2,2'-dithiophene (300 mg, 0.45 mol) and 5,5'-bis(trimethylstannyl)-2,2'-bithiophene (223 mg, 0.45 mol) with a yield of 71%.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A ratiometric vapor sensor, comprising:
a power source;
a first sensor electrically connected to the power source, the first sensor comprising:
a first semiconductor component comprising a vapor-sensitive semiconducting organic compound;
a first input electrode electrically connected to the first semiconductor component; and
a first output electrode electrically connected to the first semiconductor component;
a second sensor electrically connected to the power source, the second sensor comprising:
a second semiconductor component comprising a modified vapor-sensitive semiconducting organic compound including a modifying organic group;
a second input electrode electrically connected to the second semiconductor component; and
a second output electrode electrically connected to the second semiconductor component;
a processor that compares the voltage or current of the first output electrode with that of the second output electrode to obtain a ratio, wherein the ratio is proportional to the concentration of a vapor contacting the sensor; and
an optional enclosure for the first and second sensors that includes a gap that exposes the semiconductor material so that it can be contacted by the vapor.

2. The ratiometric vapor sensor of claim 1, wherein the first and second semiconductor components comprise a part of an organic field effect transistor.

3. The ratiometric vapor sensor of claim 1, wherein the modified and unmodified vapor-sensitive semiconducting organic compounds are in contact with a silicon dioxide layer positioned over a silicon layer.

4. The ratiometric vapor sensor of claim 1, wherein the vapor-sensitive semiconducting organic compound is a p-type organic semiconductor.

5. The ratiometric vapor sensor of claim 1, wherein the vapor-sensitive semiconducting organic compound includes an organic group selected from the group consisting of thiophene, phenylene, selenophene, fluorene, naphthalene, ethylene, ethynylene, cyclopentadiene, silacyclopentadiene, benzothiadiazole, benzoxadiazole, diketopyrroleopyrrole, and isoindigo.

6. The ratiometric vapor sensor of claim 1, wherein the vapor-sensitive semiconducting organic compound is a semiconducting polymer.

7. The ratiometric vapor sensor of claim 6, wherein the semiconducting polymer is a thiophene polymer.

8. The ratiometric vapor sensor of claim 1, wherein the first and second semiconductor components include a porogen.

9. The ratiometric vapor sensor of claim 1, wherein the vapor-sensitive semiconducting organic compound is sensitive to nitrogen dioxide.

10. The ratiometric vapor sensor of claim 1, wherein the modifying organic group is an electron-donating substituent selected from the group consisting of alkylamino, cycloalkylamino, arylamino, alkoxy, cycloalkoxy, aryloxy, alkylthio, cycloalkylthio, arylthio, alkylseleno, cycloalkylseleno, and arylseleno substituents.

11. The ratiometric vapor sensor of claim 1, wherein the modifying organic group is an electron-withdrawing substituent selected from the group consisting of nitro, cyano, trifluoromethyl, fluoro, chloro, bromo, iodo, lower alkyl keto, aryl, cycloalkyl keto, aryl keto, lower alkyl ester, cycloalkyl ester, aryl ester, lower alkyl amide, cycloalkylamide, aryl amide, phosphine oxide, alkyl phosphonate, alkyl sulfoxide, and alkyl sulfone substituents.

12. The ratiometric vapor sensor of claim 1, wherein the vapor-sensitive semiconducting organic compound is poly (bisdodecylquaterthiophene) (PQT12) and the modified vapor-sensitive semiconducting organic compound is poly (bisdodecylthioquaterthiophene) (PQTS12).

13. The ratiometric vapor sensor of claim 1, wherein the sensor comprises a display.

14. The ratiometric vapor sensor of claim 1, wherein the sensor comprises an alarm.

15. The ratiometric vapor sensor of claim 1, wherein the sensor is a wearable sensor.

16. A method of detecting and determining the concentration of a vapor using the ratiometric vapor sensor of claim 1, comprising detecting the presence of a vapor if the voltage or current of the first output electrode or the second output electrode changes, and determining the concentration of a vapor by comparing the voltage or current of the first output electrode with that of the second output electrode to obtain a ratio, wherein the ratio is proportional to the concentration of the vapor.

17. The method of claim 16, wherein the vapor is nitrogen dioxide vapor.

18. The method of claim 16, wherein the vapor-sensitive semiconducting organic compound of the ratiometric vapor sensor is a semiconducting polymer.

19. The method of claim 18, wherein the semiconducting polymer is a thiophene polymer.

20. The method of claim 16, wherein the vapor-sensitive semiconducting organic compound of the ratiometric vapor sensor is poly(bisdodecylquaterthiophene) (PQT12) and the modified vapor-sensitive semiconducting organic compound of the ratiometric vapor sensor is poly(bisdodecylthioquaterthiophene) (PQTS12).

21. The method of claim 16, wherein the ratiometric vapor sensor includes an alarm that is activated if the concentration of the vapor is above a predetermined value.

22. A vapor-sensitive sensor, comprising:
a power source;
a vapor-sensitive semiconductor component electrically connected to the power source, the semiconducting component comprising poly(bisdodecylthioquaterthiophene) (PQTS12);

an input electrode electrically connected to the semiconductor component; and an output electrode electrically connected to the semiconductor component;

a gap in a surface of the sensor that exposes the PQTS12 so that it can be contacted by a vapor.

23. The vapor-sensitive sensor of claim 22, wherein the vapor is nitrogen dioxide.

* * * * *